United States Patent [19]

Walton et al.

[11] Patent Number: 5,149,332

[45] Date of Patent: * Sep. 22, 1992

[54] ABSORBENT AND CUSHIONING PRODUCTS AND THEIR MANUFACTURE

[75] Inventors: Richard R. Walton, Ten West Hill Pl., Boston, Mass. 02114; Richard C. Walton, Wellesley; George E. Munchbach, Roslindale, both of Mass.; Robert W. Young, Locust Valley, N.Y.

[73] Assignee: Richard R. Walton, Boston, Mass. ; a part interest

[*] Notice: The portion of the term of this patent subsequent to Dec. 9, 2003 has been disclaimed.

[21] Appl. No.: 311,600

[22] PCT Filed: Dec. 8, 1986

[86] PCT No.: PCT/US86/02647

§ 371 Date: Oct. 11, 1988

§ 102(e) Date: Oct. 11, 1988

[87] PCT Pub. No.: WO88/04164

PCT Pub. Date: Jun. 16, 1988

Related U.S. Application Data

[63] Continuation-in-part of Ser. No. 754,669, Jul. 11, 1985, Pat. No. 4,627,849, which is a continuation of Ser. No. 393,543, Jun. 30, 1982, abandoned.

[51] Int. Cl.$^5$ ............................................. A61F 13/15
[52] U.S. Cl. ................................. 604/358; 604/375; 604/379; 604/385.1; 604/380; 428/152
[58] Field of Search ............... 604/385.1, 385.2, 377, 604/378, 379, 380, 358, 904; 428/152–154; 264/282; 26/18.6; 162/280–282, 425, 374, 360

[56] References Cited

U.S. PATENT DOCUMENTS

| | | | |
|---|---|---|---|
| 4,208,459 | 6/1980 | Becker et al. | 604/380 |
| 4,327,728 | 5/1982 | Elias | 604/904 |
| 4,500,585 | 2/1985 | Erickson | 604/367 |
| 4,559,050 | 12/1985 | Iskva | 604/379 |
| 4,568,341 | 2/1986 | Mitchell et al. | 604/378 |
| 4,578,070 | 3/1986 | Holtman | 604/378 |
| 4,627,849 | 12/1986 | Walton et al. | 604/379 |
| 4,688,914 | 8/1987 | Holtman | 604/379 |
| 4,704,113 | 11/1987 | Schoots | 604/379 |

Primary Examiner—David Isabella
Assistant Examiner—K. Reichle
Attorney, Agent, or Firm—Fish & Richardson

[57] ABSTRACT

In a product including at least a first layer of fibers, the layer residing in a thickened, shortened microundulated state as a result of longitudinal micro-compressive treatment, the layer is characterized by being shortened at least 20% of its original length in the direction of treatment, there being at least 10 microundulations per inch in the layer in the direction of the treatment, the compressed-together relationship achieved by the treatment being substantially preserved in said product with adjacent microundulations in said layer residing with their sides abutting one another. The microundulated layer is shape-retentive and has stored mechanical energy capable, under activating conditions, to cause the product to expand. Products, and a method of producing such products, are also described. The products include superabsorbent assemblages, tampons, pads, cushions and liquid distributing and storage articles.

53 Claims, 14 Drawing Sheets

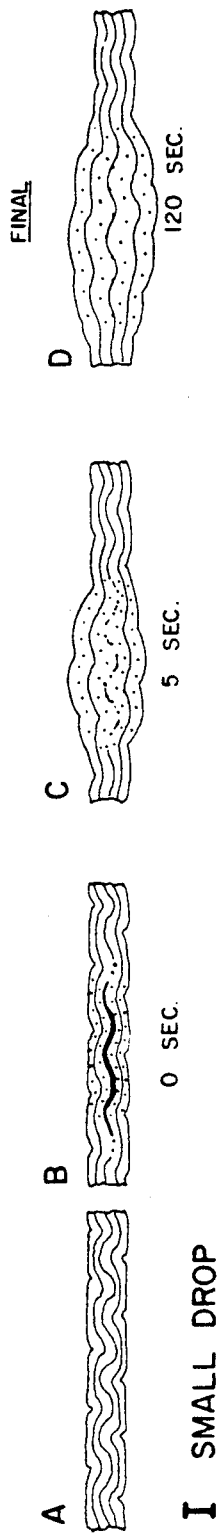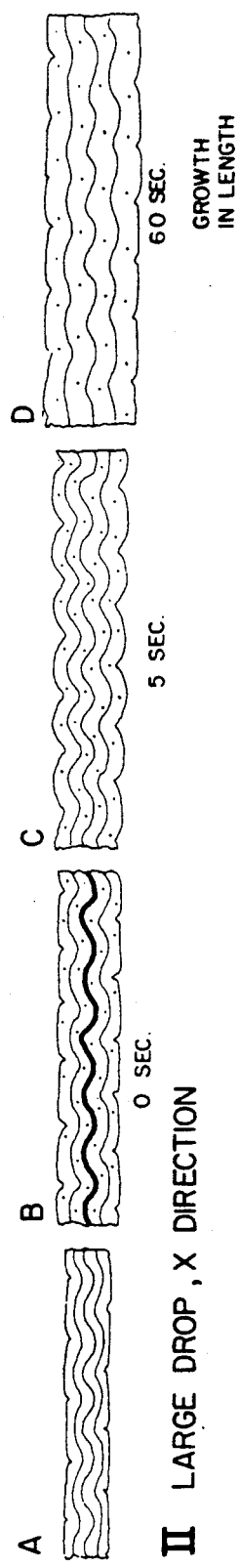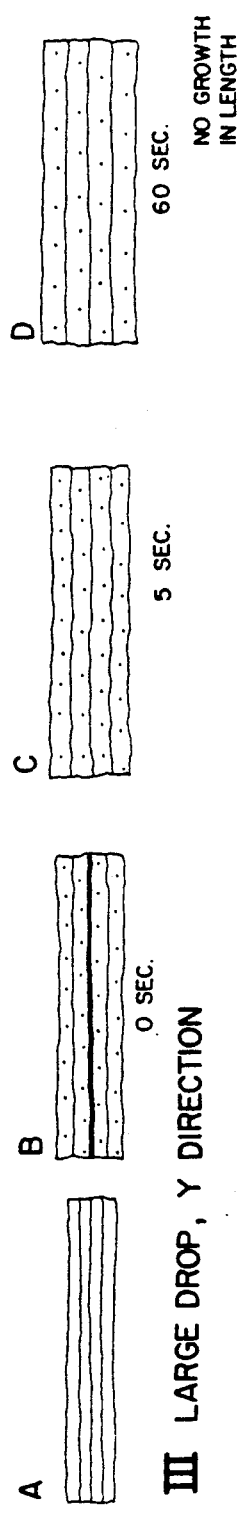
FIG. 6A — I SMALL DROP
FIG. 6B — II LARGE DROP, X DIRECTION
FIG. 6C — III LARGE DROP, Y DIRECTION UNCOMPACTED
FIG. 7
BLEACHED BLEND
MAGNIFICATION 30X
COMPACTED-COARSE
COMPACTED-FINE

S.I. RAYON

MAGNIFICATION 50X

UNCOMPACTED COMPACTED

RAYON TOW

MAGNIFICATION 50 X

UNCOMPACTED         COMPACTED

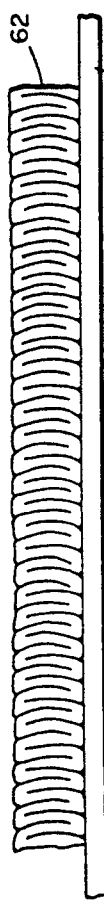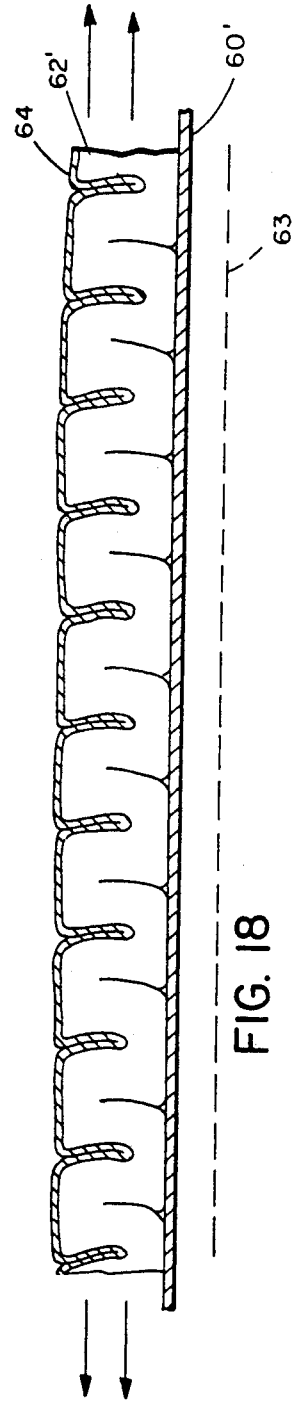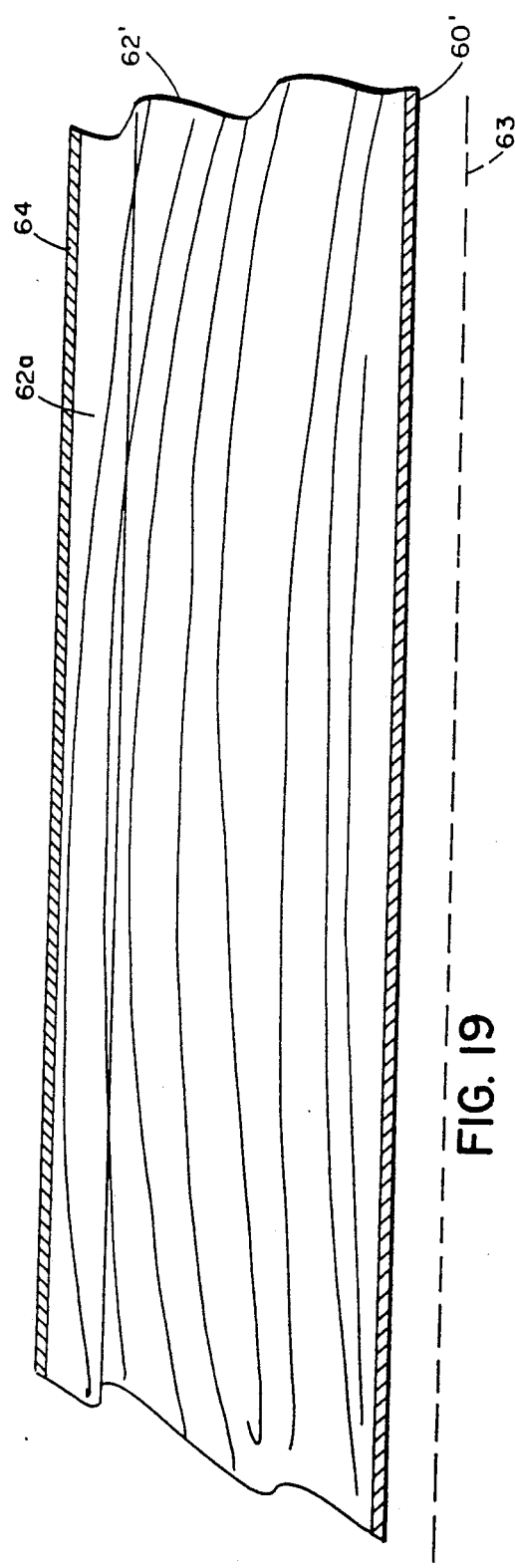
FIG. 17
FIG. 18
FIG. 19

ABSORBENT AND CUSHIONING PRODUCTS AND THEIR MANUFACTURE

This is a continuation of application Ser. No. 754,669, filed on Jul. 11, 1985, and issued on Dec. 9, 1986, as U.S. Pat. No. 4,627,849, which is a continuation of application Ser. No. 393,543, filed Jun. 30, 1982, now abandoned.

INTRODUCTION

This invention relates to absorbent and cushioning products and processes for their manufacture, in which as one step in their manufacture, the products are given desirable attributes by a longitudinal microcompressive treatment. The invention, in certain broad aspects, includes absorptive menstrual products, including tampons and pads, other products for use next to the skin for cushioning or absorption of bodily fluids, and other products which have similar requirements.

In certain aspects, the invention relates to products made of batts of long fibers such as cotton or rayon and in other aspects the invention relates to products made of inexpensive air-laid fluff pulp. The invention includes unique combinations of such materials with superabsorbent substances.

BACKGROUND

Despite decades of research by major companies in the field of absorptive and cushioning products, a basic difficulty often remains, that either the final product is objectionably bulky prior to use, or in use, it does not have the level of performance desired.

The disadvantage of large bulk may be encountered at any stage in manufacture, distribution or use. For instance, products may occupy too much space on the shelves of retail stores, in storage cabinets at home, or when carried by or worn by the user. Efforts to overcome these disadvantages oftentimes result in compromise of performance or increase of cost.

SUMMARY OF THE INVENTION

It is realized that an old technique, that of longitudinal compressive treatment of a web-form layer, by proper selection of starting materials, and by preserving its longitudinally compressed form, can lead to improved final products, in having lower pre-use bulk and better performance at practical cost. Many aspects of the invention take advantage, in use, of release of stored mechanical energy in the web, while in other aspects advantage is taken of the melding together of two layers, e.g. a fibrous distributing layer and a superabsorbent layer, during simultaneous longitudinal compressive treatment.

In another aspect of the invention, the efficiency of use of superabsorbent materials in many respects is enhanced by microcompressive treatment of the superabsorbent layer itself or of an absorbent layer combined with a superabsorbent layer.

In another aspect of the invention, a unique puff-up product is provided which enables the product to remain in dense form until use, and then, by repeated tensioning, to be rendered lofty and soft for use.

According to still another aspect of the invention, a highly dense absorbent pad is constructed which, though made of inexpensive and "dead" materials such as air-laid fluff pulp, is made capable of substantial liveliness and expansion when wetted.

According to still another aspect of the invention, products with these various attributes are produced by use of a matched serrated roll microcreper which provides bands of high density, microundulated material interspersed with bands of lesser density, microundulated material.

According to one broad aspect, the invention features a product comprising at least a first layer of fibers, the layer residing in a thickened, shortened microundulated state as a result of longitudinal micro-compressive treatment, the layer being characterized by being shortened at least 20% of its original length in the direction of treatment, there being at least 10 microundulations per inch in the layer in the direction of the treatment, the compressed-together relationship achieved by the treatment being substantially preserved in the product with adjacent microundulations in the layer residing with their sides abutting one another, the microundulated layer being shape-retentive and having stored mechanical energy capable, under activating conditions, to cause the product to expand.

Preferred embodiments of this aspect of the invention have the following features. The layer comprises long fibers in a substantially unbounded state, the shortened, compressed-together relationship being in the direction of the length of the majority of the fibers. The layer comprises a batt of substantially aligned fibers. The layer is comprised of carded fibers. The layer is comprised of rayon fibers. The layer comprises a batt of absorbent fibers combined prior to longitudinal compressive treatment with a relatively thin outer wrapping layer, the microundulations being formed in the combined assemblage. The thin layer is hydrophobic. The thin layer is adapted to puff up under tension. The layer comprises air-laid fluff pulp. Superabsorbent substance is incorporated in the layer. The layer comprises absorbent fibers, and is disposed in fluid transfer relationship with a different material.

According to another aspect of the invention, a first layer is comprised of absorbent material and superabsorbent substance is carried in a second layer, the first and second layers being in a simultaneously microundulated condition as the result of having been subjected together to micro-compressive treatment, whereby the first layer and the superabsorbent-containing layer mutually extend in intimate face-to-face relationship through a series of microundulations. Preferably the sides of the undulations abut one another, and preferably the fibers of the first layer are merged into the second layer by the treatment.

According to another aspect of the invention, a microundulated layer is disposed to permit its rapid expansion when subjected to a predetermined activating condition, preferably, again, the sides of the microundulations abutting one another.

Certain preferred embodiments of this aspect have the following puff-up features. The layer is adapted to puff up substantially in thickness in response to tensioning. Limiter means are included that limit the degree of extension of the layer during tensioning. The limiter means comprises a less extensible member joined at least at closely spaced apart points along the length of the layer. The limiter means comprises a layer intimately microcreped with the first layer after the first layer has been subjected to a microcreping pretreatment. The limiter means comprises a thin outer covering layer. The limiter means is incorporated in the body of the product. The puff-up layer is comprised substantially of polymeric fibers and the product, when puffed up, is adapted to provide a cushioning effect. The product is shaped to serve as a pillow when puffed up. The puff-up layer is hydrophobic and lies over an absorbent layer, exposed for a cushioning relationship to a part of the body, the hydrophobic layer being rapidly permeable to body fluids passing from the body to the absorbent layer. The layer is comprised of absorbent fibers and the puffing-up is adapted to enlarge the fluid-retentive volume of the layer. The product is in the form of an absorbent pad for use with the body, the product including a fluid-impermeable baffle to confine liquid to the pad. The product is in the form of a pad that is highly compact during storage and is adapted to be puffed up prior to use. The product is in the form of a menstrual pad.

Other preferred embodiments of the broad activatable aspect have the following features. The layer is comprised of absorbent fibers and the layer is adapted to expand in response to contact with fluid. The product is, or is incorporated in, a pad for absorbing fluid discharge from the body. The pad includes a fluid-impenetrable baffle along one side of the layer, the other side exposed to receive the fluid.

Still another aspect of the invention comprises improved tampons constructed with microundulated material in which the sides of the microundulations abut one another. According to one embodiment, the direction of shortening extends substantially cross-wise to the axis of the tampon, the microundulations being effective upon exposure to liquid to effect radial expansion of the outer surface of the tampon to enable interception of the menstrual discharge. In another embodiment, the direction of the shortening extends at an acute angle to the axis of the tampon, the microundulations being effective upon exposure to liquid to effect expansion of the tampon with components in both the radial and the axial direction.

According to another aspect of the invention, a product comprises multiple overlying layers of absorbent material, at least a plurality of the layers being in the thickened, shortened microundulated state as a result of longitudinal micro-compressive treatment and in some embodiments the overlying layers comprise successive turns of a prethickened, preshortened microundulated sheet-form product that has been rolled.

The invention also includes specific relationships of microundulated material in a tampon. According to one aspect, the tampon comprises, in the region of its exterior, a layer formed of absorbent fibers, the layer being in a prethickened, preshortened microundulated state as a result of longitudinal micro-compressive pretreatment prior to incorporation by subsequent compression into the form of the tampon, the layer being characterized by being preshortened at least 20% of its original length in the direction of pretreatment, there being at least 10 microundulations per inch in the layer in the direction of the pretreatment, adjacent microundulations in the layer residing with their sides abutting one another, with the length of a microundulation being generally of the order of the thickness of the prethickened layer, the microundulations of the layer being capable of distributing liquid rapidly along its extent thereby to distribute incident liquid rapidly about the tampon, the outer layer being in liquid-transmitting relationship to absorptive material lying inwardly thereof.

According to another aspect, the tampon, for absorbing menstrual discharge, comprises a web-form bat of substantially aligned absorbent fibers, the bat being in a prethickened, preshortened microundulated state as a result of longitudinal micro-compressive pretreatment by application of compressive forces acting over a short distance substantially in the direction of the plane of the batt within the cavity of a microcreper, the batt being preshortened at least 20% of original length in a given direction aligned with the length of the fibers, to a degree permitting substantial recovery of original dimension, there being at least 10 microundulations of the batt per inch of length as a result of the pretreatment prior to incorporation in the tampon, the microundulations residing with the sides of adjacent microundulations close together as a result of the longitudinal compressive pretreatment, the absorbent fibers of the batt, because of the pretreated state, having stored mechanical energy in a predetermined selected direction within the tampon determined by the orientation of the batt within the tampon, the pretreated batt as it resides in the tampon being moisture-sensitive, responsive to small amounts of liquid to expand in the given direction due to concerted release of the stored mechanical energy in the fibers whereby rapid expansion of the exterior of the tampon can occur.

And according to still another aspect, a tampon for absorbing menstrual discharge comprises a portion of web-form batt of absorbent fibers lying along the exterior of the tampon, the batt portion being in a prethickened, preshortened microundulated state as a result of longitudinal micro-compressive pretreatment by compressive forces acting over a short distance substantially in the direction of the plane of the batt within the cavity of a microcreper, the batt portion being preshortened at least 20% of original length, there being at least 10 microundulations of the batt per inch of length as a result of the pretreatment prior to incorporation in the tampon, the microundulations residing with the sides of adjacent microundulations close together as a result of the longitudinal compressive pretreatment, because of the longitudinally compressed pretreated microundulated form of the batt portion as it resides in the tampon, the batt portion having high liquid transmissivity capable of rapidly distributing liquid via the batt to portions of the tampon remote from points of incidence of the liquid upon the batt portion.

Another extremely important aspect of the invention deals more generally with constructions of superabsorbent products. An absorbent product comprises at least two face-to-face layers, the first layer formed of absorbent fibers and the second layer including superabsorbent substance, the layers being in a mutually shortened, microundulated, intimate state as a result of being subjected to simultaneous longitudinal micro-compressive treatment together.

Preferred embodiments of this aspect of the invention include the following features. The absorbent layer is adapted to receive, distribute and temporarily store a discharge of liquid and introduce it to the superabsorbent substance in accordance with the take-up rate of the substance. The product is the result of being treated by a matched, serrated roll microcreper, the product having a distribution of highly densified bands separated by bands of lesser density. The first layer comprises a paper-like layer formed of short wood fibers. The first layer comprises air-laid fluff pulp. The first layer contains a substantially larger number of microundulations as a result of a longitudinal micro-compressive pretreatment prior to being treated together with the second layer. Over the mutual extent of the layers, fibers of the first layer are merged into the body of the second layer as a result of the simultaneous micro-compressive treatment.

Another extremely important aspect of the invention deals with an absorbent pad that can be formed inexpensively and still have expansion capability. This aspect features an absorbent product comprising at least one sheet-form layer, the layer being in a thickened, shortened microundulated state as a result of longitudinal micro-compressive treatment, the layer being characterized by being shortened at least 20% of its original length in the direction of treatment, there being at least 10 microundulations per inch in the layer in the direction of the treatment, adjacent microundulations in the layer residing with their sides abutting one another, the microundulations of the layer being shape-retentive when dry with stored mechanical energy and being capable of release of mechanical energy to expand, the layer being disposed on a liquid impermeable baffle, and means establishing a predisposition of the layer to expand with a regular series of macroundulations, whereby, upon contact with liquid, the product effectively expands in thickness when wet by formation of the macroundulations due to expansion of the microundulations.

Preferred embodiments of this aspect of the invention have the following features. A liquid impermeable baffle member extends along one side of the layer, the layer being free to rise from the baffle member to form the macroundulations. The means for establishing the predisposition includes adhesive means secured to the layer in a pattern at periodic intervals preventing longitudinal motion of respective portions of the layer in the manner that the layer when wet forms itself into a series of macroundulations each in the form of a single arch between successive adhesive intervals. The means for establishing the predisposition includes a series of depression lines in the layer running substantially in the longitudinal direction of the layer in the manner that the layer when wet forms itself into a macroundulation in the form of a single arch between successive depression lines.

The invention furthermore features a method of producing an expansible article comprising selecting a web-form member comprised at least of a layer of fibers, subjecting a running length of the web-form member to longitudinal micro-compressive treatment, the member being substantially confined in the direction of its faces while compressive forces in the longitudinal direction are applied by a rotating drive element within the short cavity of a microcreper, the treatment being conducted in the manner to preshorten the web-form member at least 20% of its original length and to produce at least 10 microundulations in the member per inch of length as a result of the treatment, with the microundulations residing with their sides close together as a result of the longitudinal compressive treatment, to form a preform and thereafter forming the article with the preform in a manner that preserves in the article the close-together relationship of the sides of the microundulations.

Preferred embodiments of this aspect of the invention includes the following features. The article being formed is an absorbent pad, and the method includes combining the member with a baffle to prevent passage of liquid from the member in an unwanted direction. The article is a tampon, and the method includes inserting the preform within a compressive tampon-forming mold, and applying compression upon the preform by the mold to form the tampon. The layer comprises a batt of fibers, the fibers of the batt portion during the treatment being substantially aligned with the direction of longitudinal micro-compressive treatment. The longitudinal microcompressive treatment is accomplished by feeding the web into a nip region between two side-by-side rolls rotating respectively in opposite directions about two spaced apart axes, each roll having larger diameter segments and smaller diameter segments along its length, the larger and smaller diameter segments of the two rolls being matched to form a series of relatively shallow driving nips along a nip line alternating with relatively deep non-driving spaces, imposing by means of the larger diameter segments face-to-face compressive forces and longitudinal driving forces on the corresponding portions of the web which pass through the nips, driving web regions in the non-driven spaces by the larger diameter roll segments acting via forces transmitted through the substance of the web from the directly driven web regions to the non-directly driven web regions, and applying retarding forces on both faces of the non-directly driven regions of the web immediately as they emerge from the nip line, the retarding forces having the opposite direction to the driving forces and producing immediate, continual shortening of the emerging web, the non-driving spaces adjacent the web permitting reorientation and compaction of the non-directly driven web regions with less face-to-face compression than the face-to-face compression applied to the driven web regions, and the driven web regions being retarded indirectly by the closely disposed retarding means acting via forces transmitted through the substance of the web from the non-directly driven web regions, to cause the driven web regions to undergo their immediate longitudinal shortening. The retarding comprises slidably contacting the web on both faces of the non-directly driven web regions in the vicinity of the nip with sufficient engagement to produce the shortening.

BRIEF DESCRIPTION OF DRAWINGS

FIG. 6a–c is a graphic illustration of photographs of microundulated specimens taken during and after administration of dyed drops of water:

FIG. 7, 8 and 9 are microphotographs taken of tampon materials, namely bleached blend cotton, superinflated rayon known as S.I. Rayon, and Rayon Tow, respectively;

FIG. 17 is a magnified, diagrammatic cross-sectional view of an absorbent pad according to the invention;

FIG. 18 is a view similar to FIG. 17 of another pad having multiple layers;

FIG. 19 is a magnified diagrammatic cross-sectional view of a puff pad according to the invention, in its puffed state;

DESCRIPTION OF PREFERRED EMBODIMENTS

Figure 1D:
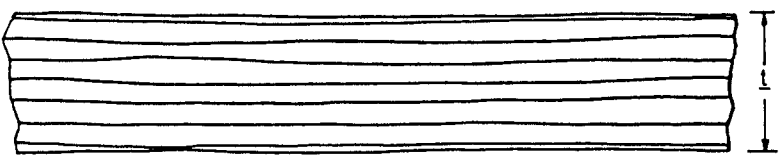
FIG. 1d for comparison is a diagrammatic view of the batt prior to longitudinal compaction in accordance with FIG. 1.
Figure 1:
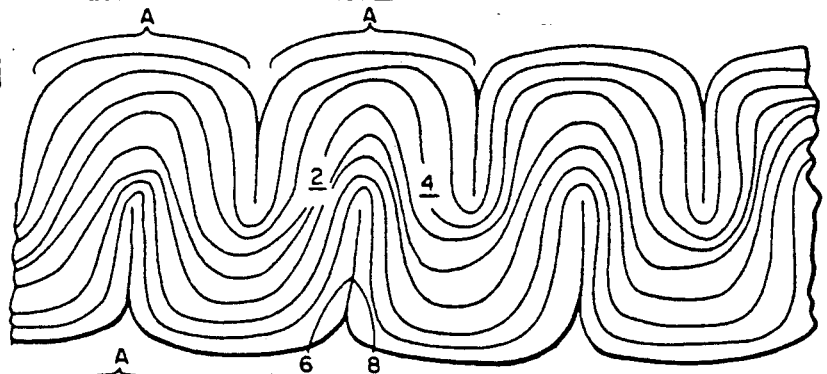
FIG. 1 is a magnified diagrammatic view in longitudinal cross section of a batt of unbonded fibers in the flat, having a series of closely adjacent microundulations as a result of longitudinal compressive treatment, the batt is shown as it comes from the longitudinal compacting device.

According to a preferred embodiment of the invention, an article is formed from a batt of substantially aligned, loose, unbonded fibers which, in its batt form, is subjected to longitudinal compressive pretreatment to provide microundulations essentially as shown in the highly magnified diagrammatic cross-sectional view of FIG. 1.

FIG. 1d illustrates the batt of loose fibers before compressive action. Such a batt may be obtained, e.g. by carding cotton fibers or rayon fibers of staple length or employing other batt forming thickness such as air layering or employing tow. The batt may have a thickness t which will vary with the weight of batt being employed. For instance, in the first preferred embodiment to be described, a batt of approximately four inch width, suitable for forming a menstrual tampon, has a weight of 10 grams per linear meter and has an uncompressed thickness t of 0.025 inch. In other embodiments such a batt may, for instance, be of 20 grams per linear meter density in the untreated state with a thickness t of 0.050 inch, or 30 grams per linear meter with an untreated thickness t of 0.075 inch.

The microundulated batt of FIG. 1 has a number of undulating ridges 2, 4 characterized by sides 6 and 8 of adjacent ridges 2 and 4 being closely adjacent to one another as a result of the application of longitudinal compressive forces. During the pretreatment, the individual fibers of the batt undergo slippage and rearrangement as the result of the longitudinal compressive action, as well as bending through the tortuous cross section as depicted in FIG. 1. The longitudinal compressive action or microcreping used to produce the microundulations is achieved by compressing the web in its own plane, in the direction of its length (direction of orientation of the fibers) by compressive forces exerted substantially parallel to the longitudinal direction of the material, while the material is confined in a small dimension treatment cavity. One means for accomplishing this action is the two-roll microcreper invented by Messrs. Richard R. Walton and George E. Munchbach, inventors herein, U.S. Pat. No. 4,142,278. An improved means is described below.

It is realized that the longitudinally compacted batt as shown in FIG. 1, if compacted to the appropriate degree, will retain its longitudinally compressed, microundulated condition so long as it is handled with the intention of preserving this form and is kept dry. This web may thus be pretreated beforehand and rolled up and stored in a roll, or it may be produced in line with a machine which makes a finished article from it.

Figure 1A:
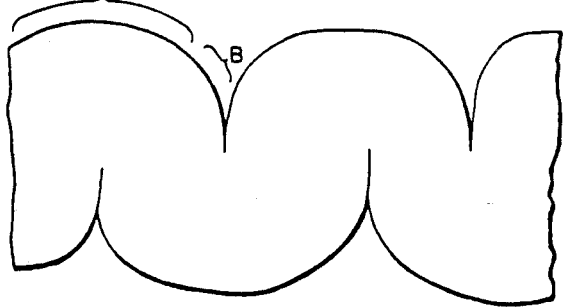
FIG. 1a is a cross sectional view similar to FIG. 1, showing the initial dynamic response of the microundulations of the longitudinally compressed batt when a treated batt of absorbent fibers is exposed to a small quantity of liquid in vitro.
Figure 1E:
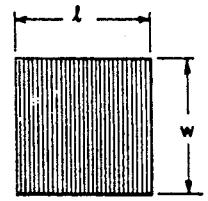
FIG. 1e is a diagrammatic plan view of a square area of longitudinally compressed batt prior to exposure to liquid with the density of microundulations suggested by a concentration of parallel lines.
Figure 1B:
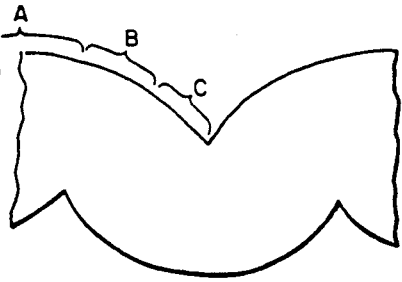
FIG. 1b is a view similar to FIG. 1a showing a further stage in the progressive expansive movement of the microundulations and progressive exposure of fresh absorptive area as expansion occurs.
Figure 1F:
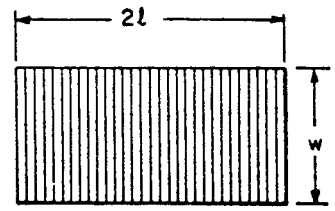
FIG. 1f is a view similar to FIG. 1d, illustrating the square area of batt of FIG. 1e after exposure to liquid, representing the extent of expansion of the batt in the lengthwise direction, by the increased spacing of the parallel lines, no expansion in the widthwise direction having occurred.

FIGS. 1a, b and c and the graphic representation of photographs of an actual experimental demonstration, FIG. 6, (described in detail further below) illustrate the reaction of such a microundulated batt in vitro to exposure to liquid, as an indication of the behavior of this web when incorporated in a finished article. FIG. 1a and Series I of FIG. 6 show the effect upon the microundulated batt of exposure of the batt to only a small amount of liquid. The tightly compressed microundulated structure swiftly responds in two ways. As demonstrated in FIG. 6, stage C of Series I (5 seconds after application of the liquid), the immediately adjacent fibers rapidly conduct liquid to adjoining fibers so that there is an immediate and uniform liquid distribution throughout a large area of the treated batt, much more so than if the batt were untreated, due to the closeness and unique interengagement of the rearranged fibers as the result of their preserved microundulated condition. Secondly, as demonstrated by comparison of Series II with Series III of FIG. 6, the contacting liquid initiates the release of the substantial stored, directional mechanical energy that has been set into the mass by the microcreping process. It will be seen that the web expands in one predefined direction as the small microundulations or ridges begin to relax and move. The individual fibers in exposed region, A, move in a dynamic way, adjusting the relationship between individual fibers and providing, though slight, a disturbance to the fluid that seeks to enter. This may be of importance in the case of menstrual pads or tampons made from the treated batt, because the menstrual fluid includes cells, blood and secretions that tend to mat and coagulate and to some extent block the flow of liquid into the absorbing structure. The dynamic fiber action may aid in the movement of this fluid into the interior. Furthermore, by comparison of FIGS. 1 and 1a, it is seen that during the absorptive process, additional fresh absorptive area, B, has been exposed. This action continues as illustrated in FIG. 1b in which, after application of still more fluid, still further fresh absorptive area, C, is exposed. This uncovering of fresh fiber surface reduces the blocking effect of secretions by presenting a greater surface area for liquid transfer.

Figure 1C:
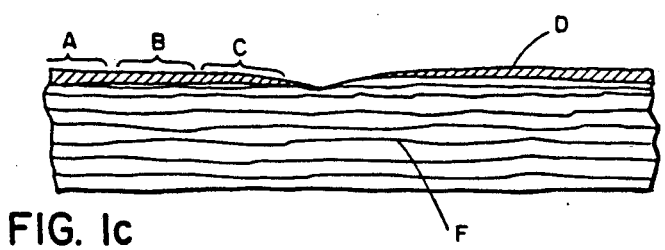
FIG. 1c is a view similar to FIGS. 1a and 1b, showing the batt when expansion of the microundulations is complete.

In FIG. 1c is shown the ultimate full extension of the microundulated batt almost to its full original length, as a result of the ultimate release of the stored unidirectional mechanical energy. (To similar effect is stage D in Series II of FIG. 6.)

For illustrative purposes in FIG. 1c, varying thicknesses of accumulated material D are shown in the areas corresponding to areas A, B and C to symbolize the variation in matting that may occur in actual use due to the progressive exposure of fresh surface. Also, a certain kinkiness is shown remaining in the individual fibers, F, in FIG. 1c, as a result of the longitudinal compressive treatment in gross of the batt of fibers. This contributes interstitial volume to the mass that can add to the absorptive effects of the finished article.

Various batt materials respond somewhat differently to the longitudinal compressive treatment process, so that while preserving the ability of substantial dimensional recovery, different amounts of longitudinal compaction are appropriate. A preferred material is a batt of staple rayon with the fibers aligned essentially in the longitudinal direction of the batt, (though the fibers may be somewhat mechanically interengaged, e.g. if carded). It is presently preferred to compact this batt 50%, at is, to shorten the batt by one half and increase its lineal density twofold by the microcreping process. In the case of bleached cotton, which has a somewhat more resilient nature, and as well a greater portion of fibers which are not entirely aligned with the longitudinal direction of the batt, the degree of preferred compaction is less, e.g. in the 25 to 30% range.

In general, it is found that a useful degree of the longitudinal compaction in batt form can be applied to most common absorbent fibers, the range of useful preshortening being between about 20% to 60% of the original length of the fibers in the case of carded fibers.

The number of microundulations to be formed to take advantage of this aspect of the invention will vary with the nature and thickness of the material and the circumstances of intended use, but the batt must have microundulations, i.e. there must be at least 10 or more undulations per inch, and these must be compacted together, with sides of the microundulations being closely adjacent to one another, in order to generate a useful force of expansion as described herein.

By way of example, we refer to the use of the microundulated batt in the making of menstrual tampons. In the preferred case of using a thin, 10 gram per linear meter, four inch wide, untreated density batt, e.g. for forming the exterior of a tampon about an insert, preferably as many as 40 microundulations per inch are employed and the preferred minimum number of microundulations is about 25. For a 20 gram per linear meter batt, the most preferred number is about 30 and the preferred minimum is about 20 microundulations per inch. In the case of a batt of 30 grams per linear meter untreated density (which might be the only absorptive constituent of a tampon) the most preferred number is 25 microundulations per inch and the preferred minimum is about 15 microundulations per inch. These numbers refer to the number of ridges to be produced prior to introduction into the tampon mold. Further compaction in the compressive tampon mold increases the density of the ridges of microcreping substantially.

Forming The Microundulated Web With A Matched Serrated Roll Microcreper

Figure 3:
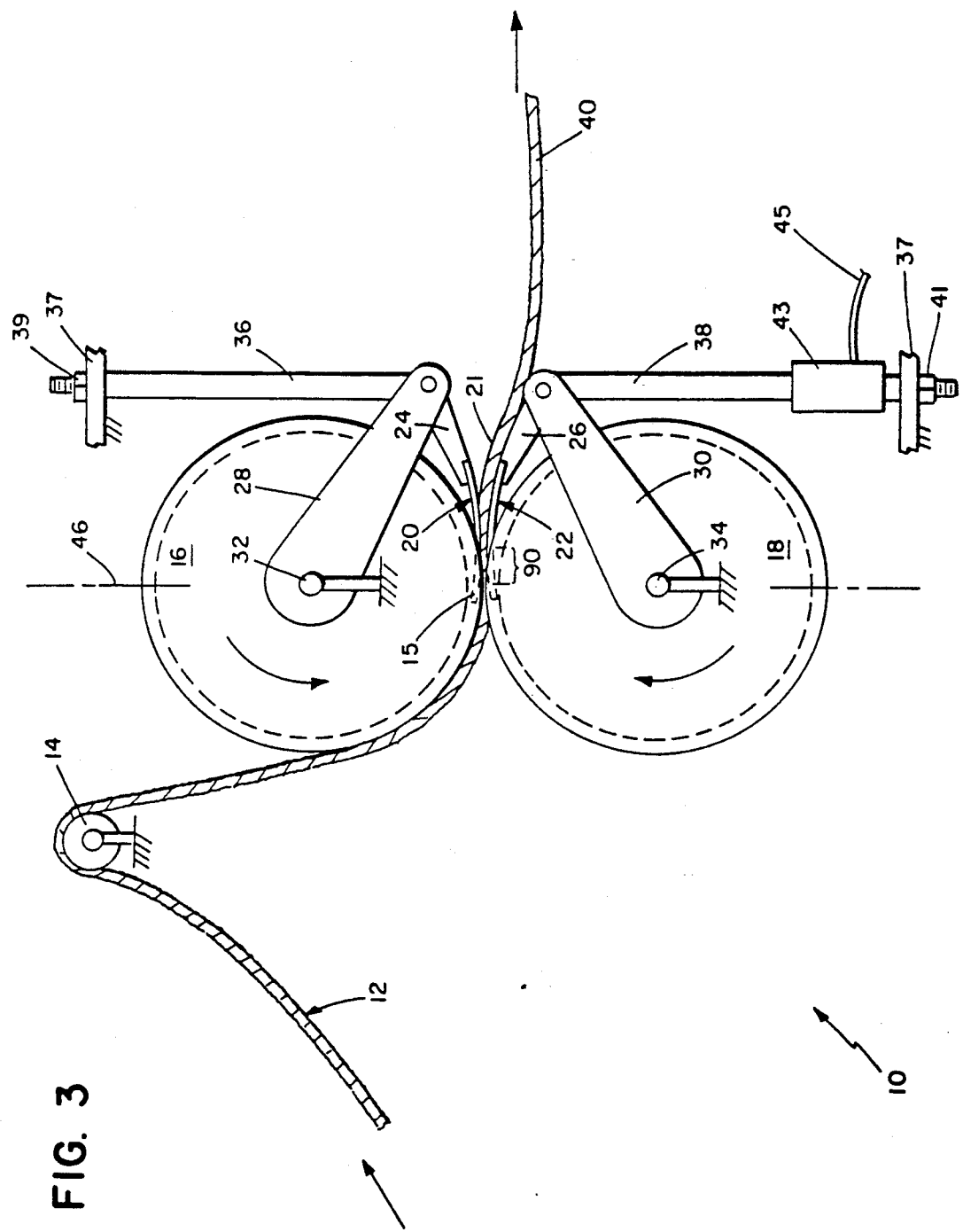
FIG. 3 is a side view of the microcreper of FIG. 2.

Referring to FIG. 3, the continuous web 12 is led from a supply roll (not shown) over a guide roll 14 into the nip region 15 between two drive rolls 16, 18 that are driven at the same speed in opposite directions (as indicated by the arrows). On the outfeed side, a pair of retarders 20, 22 (one of which includes a dwell plate 21) are positioned to retard the motion of web 12 in a manner to be described in more detail below. The processed web 40 is delivered to a take-up conveyer in a manner that carefully preserves the compressed-together relationship of the microundulations.

Each roll 16, 18 is milled to form a succession of identical, larger diameter (4 inch) disks (segments) 50 alternated with a second set of identical disks (segments) 52 of somewhat smaller diameter ($3\frac{1}{4}$ inch) than disks 50. At the nip region, each roll 16, 18 thus presents a series of alternating lands (formed by the peripheral surfaces of the larger disks 50) and valleys (formed by the peripheral surfaces of the smaller disks 52). The respective axial positions of rolls 16, 18 are matched, that is the lands of roll 16 are opposite the lands of roll 18 and the valleys of roll 16 are opposite the valleys of roll 18.

Figure 4:
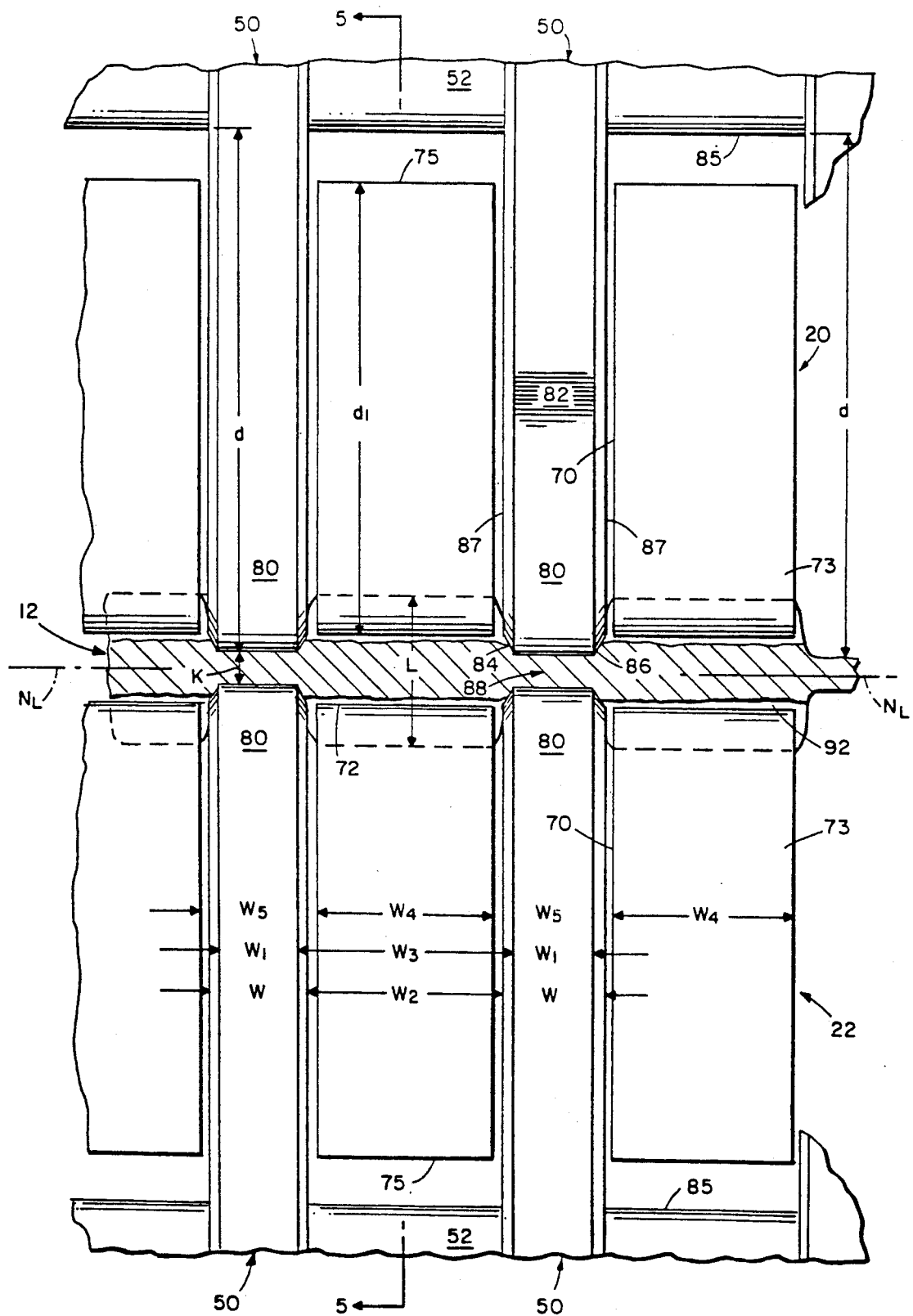
FIG. 4 is an enlarged view from the infeed side of a representative portion of the nip of the machine.

Referring to FIG. 4, each of the two retarders 20, 22 is cut from a sheet of $\frac{1}{4}$ inch thick metal to form a row of parallel, evenly spaced retarder fingers 70. Each finger 70 has a contact surface 72 that slidably contacts one face of the web and an end face 73 that is substantially perpendicular to the plane of the web. The width $W_4$ of each finger 70 (e.g., 0.090 inch) and the width $W_5$ of the space between adjacent fingers 70 (e.g., 0.060 inch) are such that successive fingers 70 nest within successive valleys along the corresponding roll 16, 18. Each retarder 20, 22 is rolled to have a radius of curvature of about 4 inch along the length from retarding face 72 to the brackets 24, 26, with the two retarders curving away from each other toward their bracketed ends. Fingers 70 are relatively rigid. Dwell plate 21 (a 0.020 inch thick blue steel plate that is coextensive with retarder 20 in the direction of the roll axes) is welded along one of its edges to the bottom face of retarder 20, at a distance of about 2 inches from the nip. The precise location of plate 21 relative to the nip, for a given treatment of a given web, is determined by trials by moving the plate in and out until the best performance is obtained. The bottom surface of plate 21 and the upper surface of retarder 22 and its support define a dwell cavity whose function is described in greater detail below.

Referring to FIG. 4, each finger 70 has a depth $d_l$, (e.g., ¼ inch) that is about two-thirds the depth d (e.g., ⅜ inch) of the valley in which it nests. Each larger diameter disk 50 is machined to have a central peripheral driving track 80. The total width, W, of disk 50 is, e.g., 0.050 inch, the width, $W_l$, of the track 80 is between 0.025 inch and slightly less than 0.050 inch (e.g., 0.045 inch), and the total space, $W_3$, between tracks is between 0.100 inch and 0.150 inch (e.g., 0.110 inch). Track 80 is cylindrical, its surface is parallel to the roll axes 32, 34, and it bears a friction surface formed, e.g., of parallel knurling spaced at intervals of, e.g., 80 lines per inch. The friction surface is chosen to enhance the drive capability of the nip while still permitting the driven portions of the web to slide upon the roll surface when it is shortened in the treatment cavity. On either side of track 80 is a smooth convex shoulder 84, 86 which is contoured to meet the side surface 87 of the larger diameter disk 50. Corresponding lands of the matched rolls 16, 18 thus form (a) a series of relatively shallow driving nips 88 along nip line $N_L$, in which the web 12 is pinched (compressed by face-wise forces) and driven by longitudinal forces toward the outfeed side, and (b) an intervening series of relatively deep non-driving spaces 92 between successive driving nips. Non-driving spaces 92 provide space on both sides of web 12 for its reorientation and compaction. The retarders 20, 22 are positioned at the outfeed end of non-driving spaces 90 and resist the motion of web 12.

Figure 5:
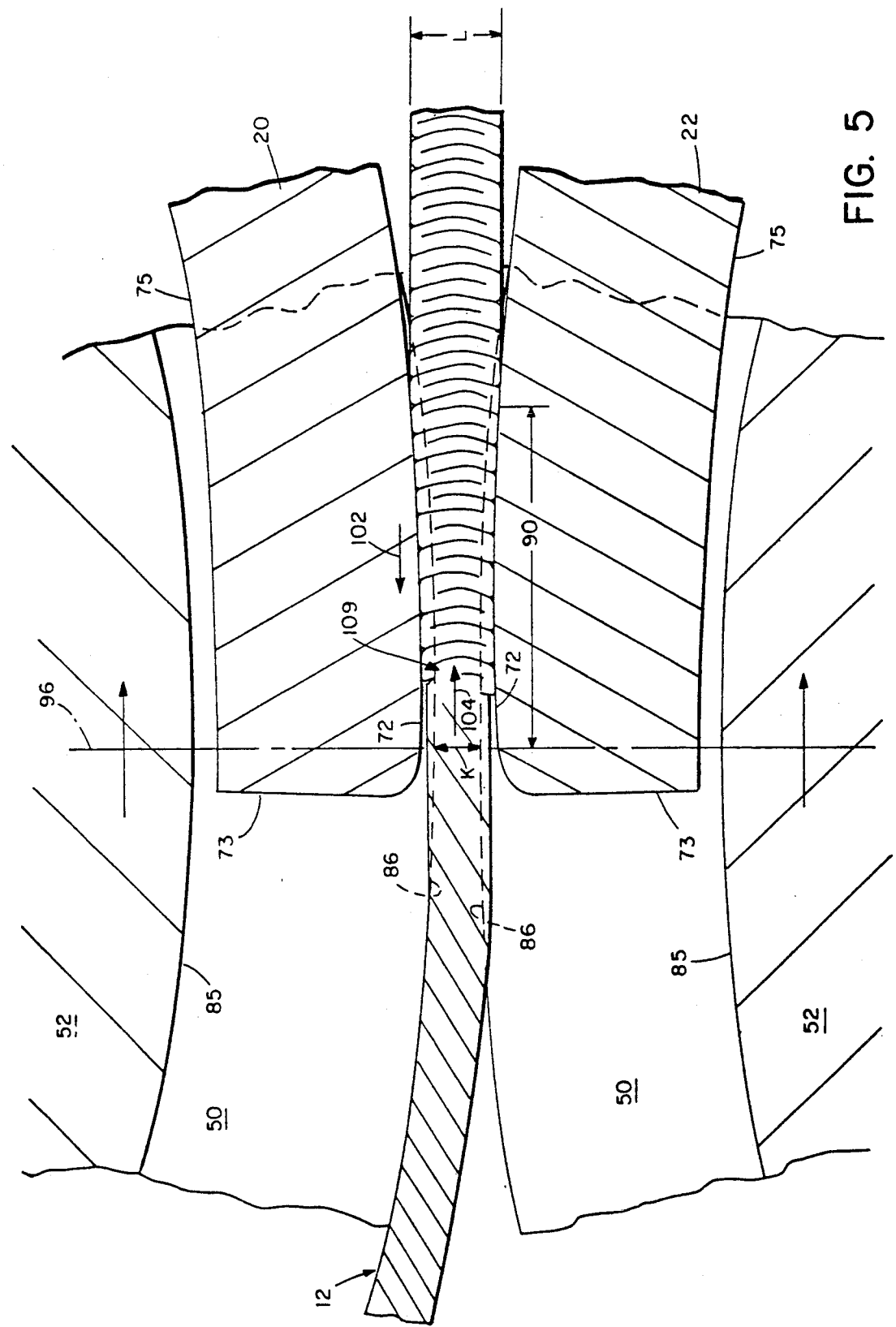
FIG. 5 is a diagrammatic, side sectional view taken at 5—5 in FIG. 4.

Referring to FIG. 5, the processing of web 12 occurs in a short length region 90 beginning approximately at the nip region of the two rolls (here on the plane 96, on which the axes of roll shafts 32, 34 lie) and ending at a point a short distance (i.e., a distance far shorter than the radius of either of the roll 16, 18) on the outfeed side slightly beyond the point of contact of the web with the retarding fingers. The processing is accomplished by the driving forces applied at the driving nips and the interdigitated retarding forces applied at the non-driving spaces, combined with the configurations of the driving nips, the non-driving spaces, and the retarders, and the positioning of the retarders relative to the rolls.

Within each non-driving space 92, the fingers are positioned in the nip region. The precise position will depend on the thickness of the web being processed and on the fineness of the microcreping desired. A thicker web will require a greater space between the opposed fingers and a smaller space will produce a finer microcrepe. The best position is determined by trials at different settings for a given web and desired treatment.

Figure 2:
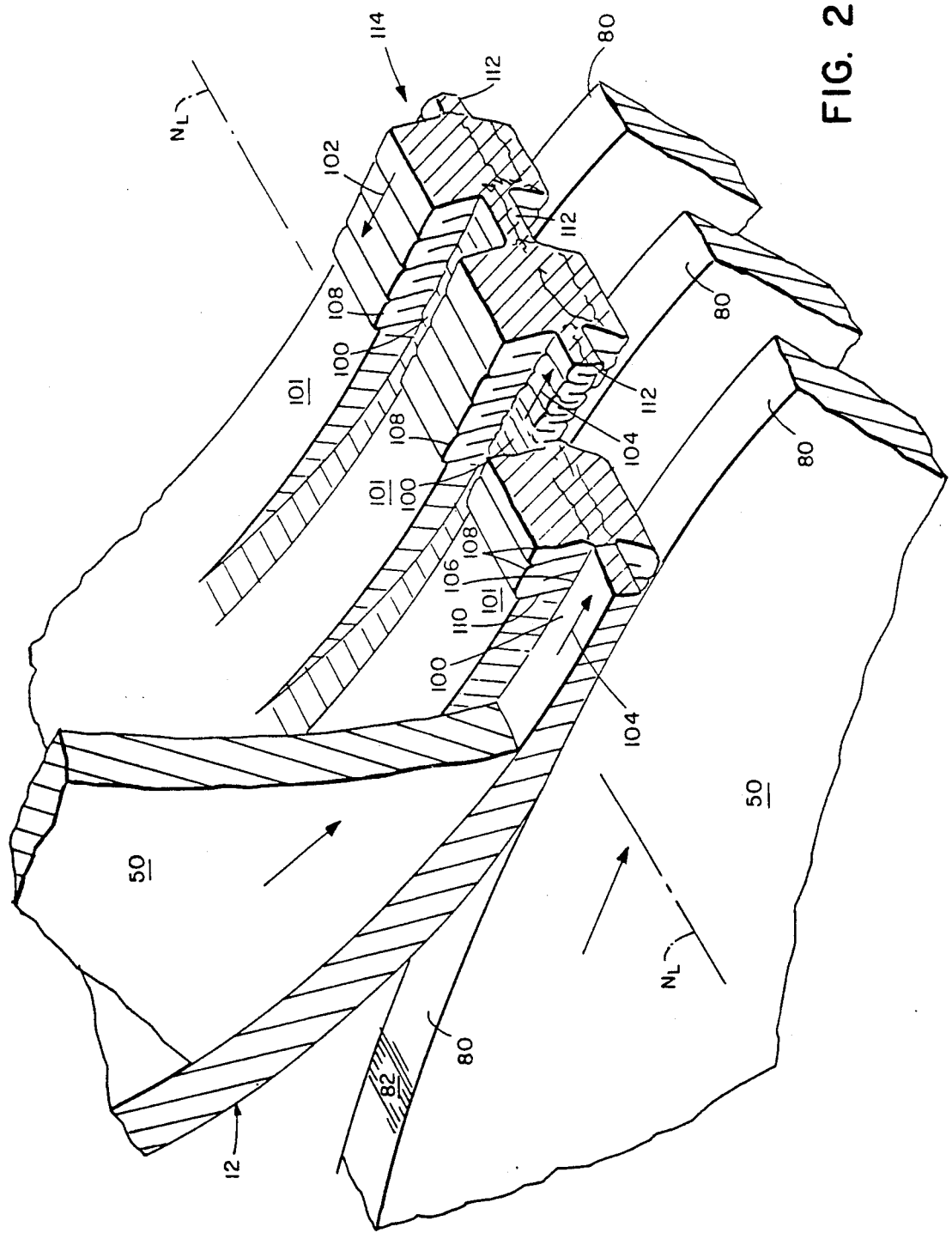
FIG. 2 is a diagrammatic perspective view of a microcreper having a matched pair of serrated rolls treating a batt of unbonded fibers, with parts broken away.

Referring to FIGS. 2, 4 and 5, in operation, web 12 is driven forward through the nip region toward the outfeed side along a series of narrow parallel strips (driven portions) 100. As web 12 reaches the nip region, the web is compressed facewise (perpendicular to the plane of the web) along strips 100 within driving nips 88. The friction surfaces (e.g., the knurling) of the tracks 80 grip the compressed strips and drive them toward the outfeed side, arrows 104, FIG. 5. At the same time the non-driven regions of the web that enter the non-driving spaces are free to remain relatively less compressed facewise (in the direction perpendicular to the web) because of the space available in the non-driving channels above and below the web. When the web reaches the retarding fingers 70, the driven strips 100 continue to be driven forward by the driving force (arrows 104), but the non-driven regions 101 receive retarding forces (arrows 102) in the opposite direction to the driving forces. Forces 102 are imposed by virtue of the relationship of the surfaces of the retarding fingers to the corresponding face of the web. In the transition regions 106 between the driven strips 100 and the non-driven regions 101, the web (by virtue of intertangling of the fibers, in the case of a bat) transmits at least part of the driving forces indirectly to the non-driven regions which causes reorientation and compaction of the non-driven regions within the treatment cavities 109 that are defined by the retarding fingers. As the driving continues, the non-driven regions are compacted in the longitudinal direction of the web, and substantially reoriented.

The non-driven regions form a succession of tightly packed undulations. Their outer portions at the faces of the webs are restrained due to frictional drag of the retarders while the inner portions are displaced forward due to the drive forces applied by the adjoining portions of the web. Thus the undulations in strips 101 take a distorted form, which can be referred to as lazy "U's", 108, as shown in FIG. 2. The vertical space between retarders 20, 22 provides an escape pathway for the undulations such that the driving force transmitted from strips 100 propels them in succession between the retarders, with the sides of the undulations in contact.

The compaction of the non-driven regions along the longitudinal direction of the web means that the processed web is relatively shorter than the unprocessed web and exits the outfeed side at a slower rate than it is pulled into the nip region. It is found that the entire web, both the driven strips 100 and the non-driven portions 101, is generally delivered at the outfeed side at the same rate and with the same degree of shortening. Just as the transition regions 106 of the web, under tension, transmit the driving forces from driven regions 100 to the non-driven regions 101 to accomplish compaction of regions 101, the transition regions, under the same tension, transmit the retarding forces 102 from the non-driven regions 101 to the driven strips 100. As the lazy "U's" 108 are formed in the non-driven regions, compaction and microcreping of the driven strips also occurs at the outfeed end the driven strips to form a series of parallel transverse compressed microcrepes 112 of lesser height and higher density, which may slope in the opposite direction.

Types of Bat

Carded batts of cotton or rayon fibers can readily be employed in the manufacture of menstrual pads or tampons according to the invention, but the invention is not so limited. For instance, using a two roll microcreper according to U.S. Pat. No. 4,142,278, a batt or array of monofilaments, e.g., so-called "tow", can be treated as a batt by being passed through the microcreper to produce microundulations in an ordered manner to the assembly. This can avoid the step of carding, and as well, in some cases, can avoid the need of a prior step to crimp the fibers in the fiber-making process.

Experimental Demonstration of Properties of Efficient Liquid Transfer and Expansion in Preferential Direction (FIG. 6)

The effects of liquid are illustrated on sample segments of a batt of normal tampon material (bleached blend cotton) which has been treated to have the microundulations that have been described. This batt, composed of a number of superposed carded layers, was processed as a unit through the two roll microcreper, referred to above, to achieve the microundulated condition. The drawings of FIG. 6 are representative of actual photographs taken using water containing dye (fast green FCF histological dye, National Aniline Division, Cenco Central Scientific Co.).

In series I of the tests, at stage A the machine direction edge of the specimen is shown prior to introduction of liquid. The microundulated structure is visible and the make-up of the web by a number of carded layers is suggested. A one microlitre drop was then applied to the edge of the specimen and simultaneously the photograph of stage B was taken. It is seen that the small drop, immediately upon application, is mostly concentrated in central carded layers of the microundulated sheet, corresponding to the point of application, but as suggested by the stippled area bounding the dark area, some liquid has entered adjacent layers. As seen ar stage C, within only 5 seconds of application, very uniform spreading of the liquid has occurred, close to the final degree of stage D taken at 120 seconds after application of the liquid.

Series II and III of FIG. 6 show respectively the effect of a larger drop of the dyed liquid on identical specimens, except that series II views the profile of the specimen in the machine direction, the same as FIG. 1, in which the microundulations are seen, direction X, while series III shows the specimen in the cross-direction, Y, taken along the length of one of the microundulations of the specimen. The large drop was formed by the dipping of a glass rod into the liquid and allowing the first drop to enter the specimen. Stage A is the specimen prior to administration of the drop, stage B represents the specimen immediately upon application of the drop, stage C represents the state of the specimen five seconds after the application of the drop, and stage D represents the state of the specimen 60 seconds after application of the drop. Both specimens were approximately 8 mm square prior to application of the liquid. As suggested by the drawing, the specimen of series II grew in the X direction to the stage D size of 10.4 mm, largely obtained within the first 5 seconds of application of the liquid, whereas as shown in series III, no growth in the Y dimension was observed. In both cases the web was seen to grow significantly in thickness, as illustrated.

Figure 8:
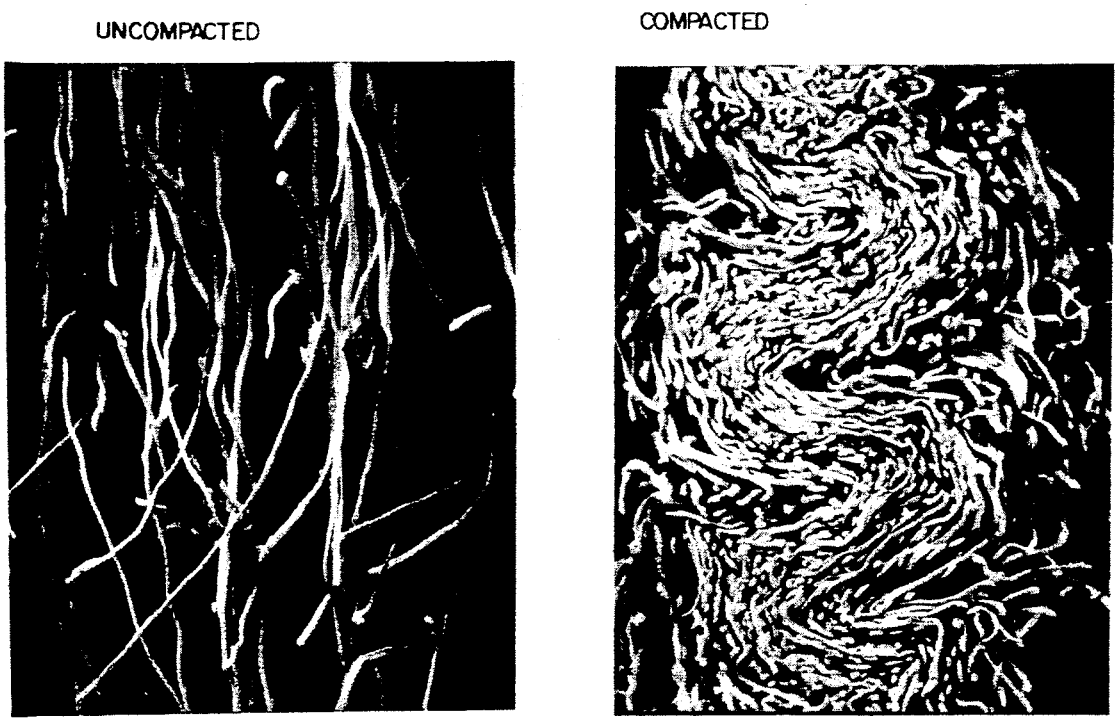
Figure 9:
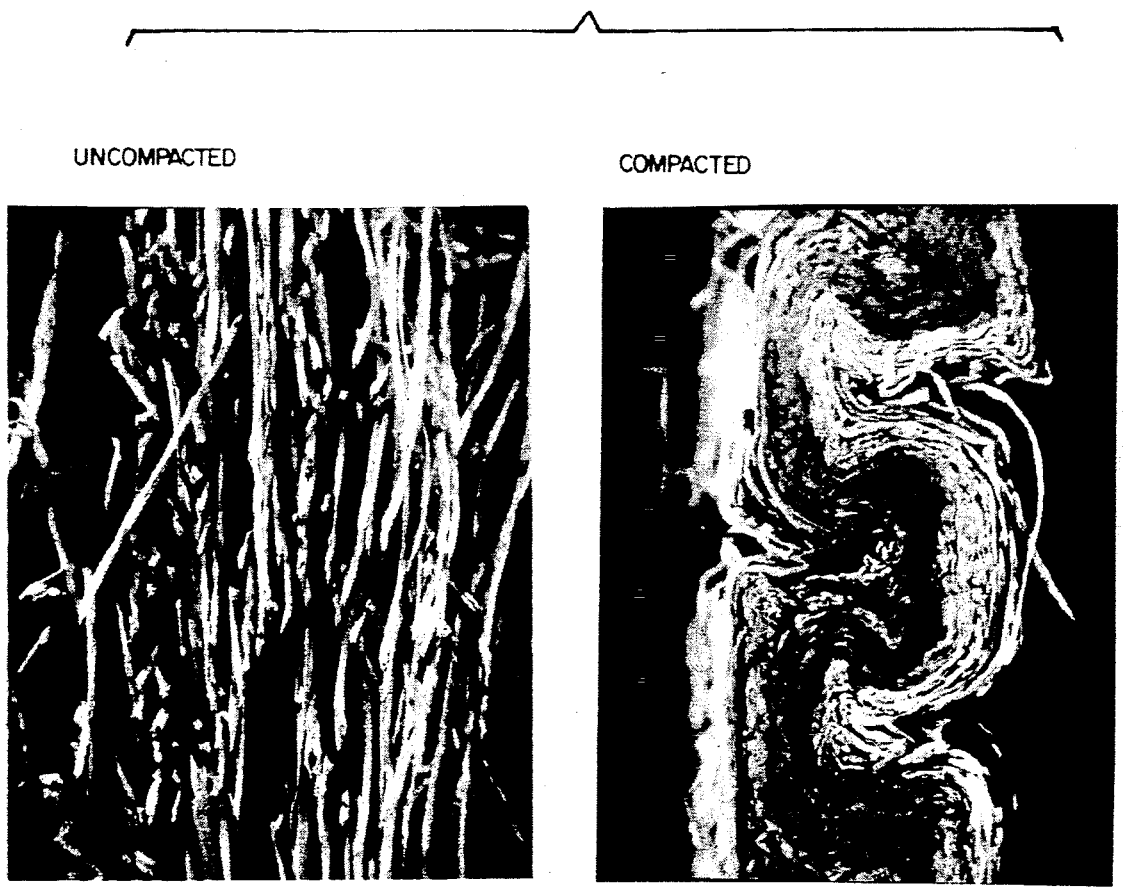

Electron Microscope Photographs of Menstrual Pad and Tampon Materials (FIGS. 7-9)

The photographs shown in FIGS. 7 through 9 were taken at the magnifications indicated, employing a scanning electron microscope (J.O.E.L.-J.S.M.15). Each specimen was cut from a sheet and sputter-coated with gold palladium alloy under approximately 160 microns vacuum using a sputter coater. The coating thickness of about 300-400 angstroms was achieved by a number of successive coatings. The FIG. 7 photographs are of bleached blend cotton, all taken at 30 times magnification, of the edge of respective specimens. The photograph of the uncompacted material shows the fibers mainly aligned in the vertical direction, i.e., the machine direction, with no regularity to the bends that occur in the individual fibers. The other two photographs, of coarse and fine microundulated materials, show a regularity to the configuration of the fibers in the microundulated form described above.

FIGS. 8 and 9 similarly show the microundulated change in the fibers in the respective materials, carded rayon batt (denoted S.I. Rayon) and rayon tow.

Figure 11:
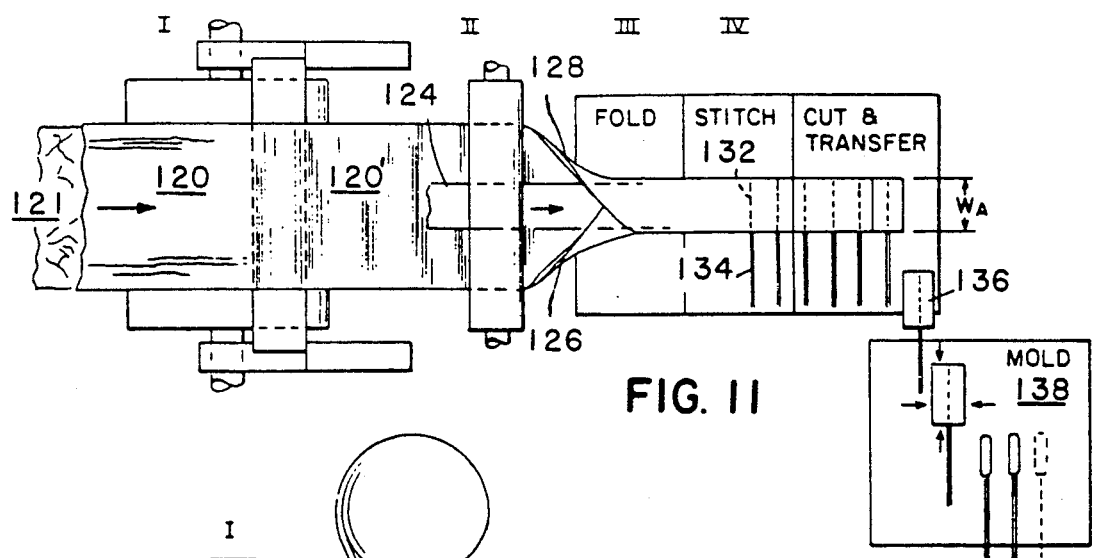
FIG. 11 is a plan view of the apparatus of FIG. 10.
Figure 10:
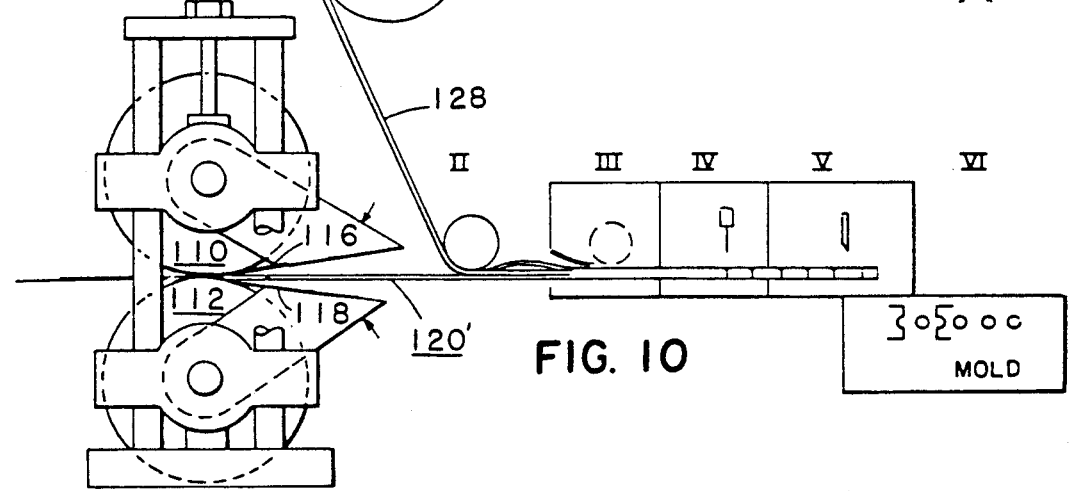
FIG. 10 is a side view of apparatus for pretreating the batt and subsequently forming a tampon according to one preferred embodiment of the invention.

FIGS. 10–11 illustrate the manufacture of a preferred tampon. At station, I, a two-roll microcreper receives an untreated batt 120 of carded tampon-forming fibers, which are essentially unbonded to each other and generally aligned with the machine direction. This batt 120 lies upon a nonwoven hydrophilic tampon outer layer 121, typically a bonded cellulosic fabric of about 0.003 inch thickness as used in the trade. The microcreper employs a drive nip for driving the batt along a path formed by a pair of oppositely rotating drive rolls, 110 and 112 in FIG. 10. A retarding device on the exit side of the nip is formed by at least one and preferably two relatively stationary retarding members 116 and 118.

The material begins to slip on the rolls and compresses longitudinally in the treatment cavity formed by the surfaces of the rolls. The resistance that leads to this compression is provided by the two retarding members 116 and 118. In this case of the batt of fibers of the present invention, the fibers are formed into microundulations in the form shown in FIG. 1 in which adjacent ridges of the microundulated structure tightly abut one another in the treatment cavity as a result of the longitudinal compressive forces applied. In general, as mentioned above, there will be at least 10 microundulations per inch for even the thickest material that might be employed in a tampon and typically more depending upon the thickness of the batt being treated and the nature of the material selected.

From this treatment the web is led either to a temporary storage roll or to the further tampon-making equipment, with care being observed to avoid substantial tension to avoid stretching, thus to preserve the close adjacency of the ridges of the microundulations.

In the preferred embodiment, as mentioned before, the batt 120 of fibers is comprised of carded rayon staple fibers, 10 grams per meter, and it, together with the thin outer layer 121, is compressed 50% by the microcreper, i.e., it is shortened by half and its weight after treatment is 20 grams per meter. At station II in the machine of FIG. 10, an unmicrocreped insert layer 128 of hydrophilic material, preferably an insert of carded bleached blend or of highly absorbent carded staple rayon fibers, having a weight of 40 grams per meter, is introduced. This insert layer is only about one third as wide as the microcreped layer 120. In the most preferred embodiment this material is so called S. I. Rayon, staple fiber obtainable from Courtaulds, Ltd., of Manchester, England. This insert layer 128 is applied to the middle of the pretreated batt 120' as depicted in FIG. 10. At station III, as shown, edge 126 of the microundulated sheet is folded over the insert to provide a folded assembly. At stage IV, the tampon-end of the withdrawal string is secured across the width of the assembly by stitching 132. A free length 134 of the string extends beyond the assembly. At stage, V, a tampon blank of 1 ¾ inch length in the axial direction of the batt is cut from this continuous assembly, the width $W_A$ of the batt and insert assembly being in the folded condition about 4 inches. This tampon blank 136 is moved sideways relative to the machine direction into the tampon mold 138.

Figures 12, 13:
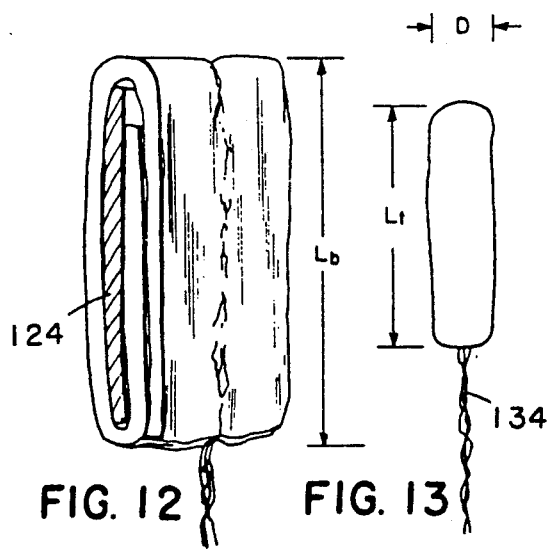
FIG. 12 is a perspective view of the tampon blank prior to insertion into the compressional forming mold.
FIG. 13 depicts a finished tampon after it has been subjected to the tampon-making steps.

FIG. 12 suggests the tampon blank 128 as it enters a conventional tampon-making compression roll which compresses the blank radially and axially and FIG. 13 suggests the relative size of the finished tampon.

Figure 14:
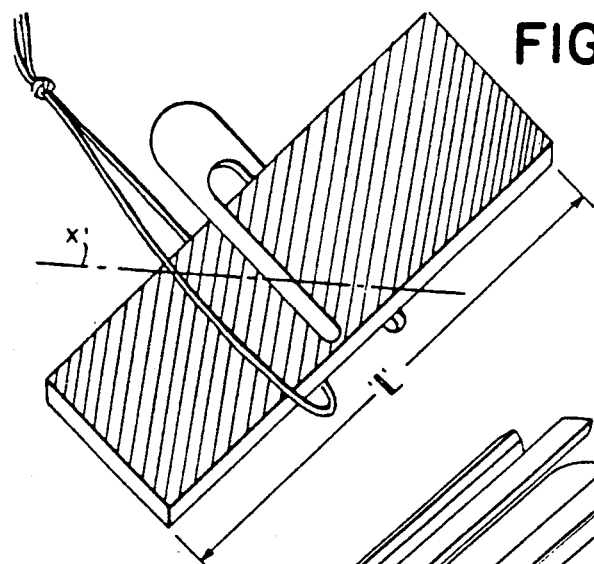
FIG. 14 for another embodiment, depicts a microundulated tampon blank for use in making a tampon by a rolling method.
Figure 15:
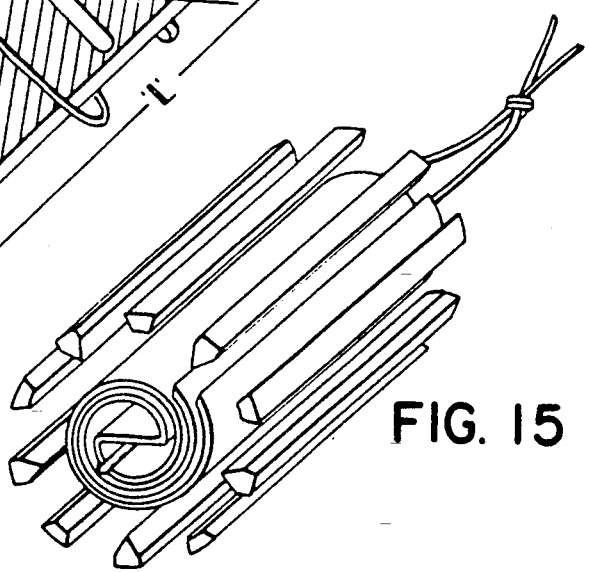
FIG. 15 shows the rolled tampon blank inserted in the tampon-making die and FIG. 16 shows the finished tampon in accordance with this embodiment.
Figure 16:
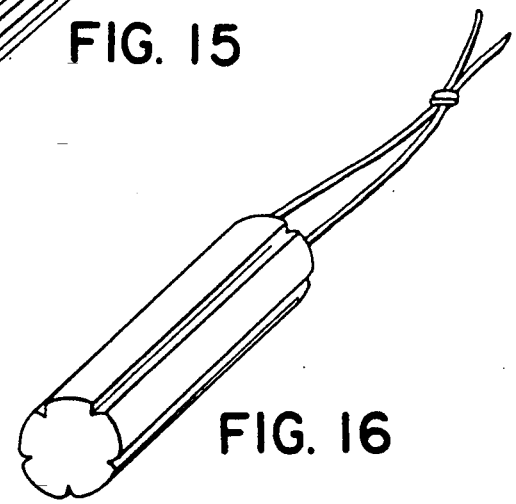

FIGS. 14, 15 and 16 illustrate the making of a tampon of rolled form using a different type of mold. In FIG. 14 is shown a tampon blank comprising an elongated strip of fiber batt, and, as suggested by the diagonal lines, the pretreatment under longitudinal compaction has occurred on the diagonal axis $X'$. This may be accomplished by cutting the specimen on the bias from normal transversely microundulated batt as produced by the machine described above. The tampon blank in FIG. 14 is initially rolled into a cylinder as shown in FIG. 15 and inserted within a radially acting die which compresses the roll to the final tampon form as shown in FIG. 16. The diagonal direction of the microcreped ridges of the microundulations thus exist in the resultant tampon.

When exposed to liquid, the diagonal nature of the compacted ridges produces an expansion at right angles to the lines of compression. This effects a component of longitudinal as well as radial growth in the tampon as part of the expansion. In tampons previously formed using the general procedure illustrated in FIG. 15, there has been difficulty because, when exposed to menstrual fluid, the tampons at times become too large in diameter and are uncomfortable to remove. The diagonal arrangement as described herein enables some of the growth to be expressed axially, thus reducing the total radial growth of the mass. This may improve the removability of the tampon. Furthermore, by precompressive longitudinal treatment of the web, the roll size required to be introduced into the die of FIG. 15 may be of reduced dimension.

Absorbent and Cushioning Pads

Referring to FIG. 17, a pad is shown comprising a sheet-form support 60 upon which is carried a microundulated web 62 in which the sides of successive undulations abut, i.e., are retained in close proximity to one another, to preserve as much as possible the original form after the compression forces of manufacture have been relieved. While such an abutting relationship can be more or less obtained, the precise degree to which this is possible depends upon a number of factors, such as the nature of the substance of the web, its thickness, the settings of the machine, the temperature of processing and the length of time in which the microundulated web is subjected to constraint during its treatment. In the case of certain webs, it is desirable to employ the dwell cavity defined by dwell plate 21 in FIG. 3.

The advantages of such a product as depicted in FIG. 17 vary depending upon the application. Where the support 60 is liquid impermeable, and the fibers of web 62 are absorbent, the product may be, by itself, an absorbent pad or it may be a constituent of one. It may be preformed, wound, and sold in roll form to converters.

Where the layer 62 is formed of cotton or rayon fibers it may be employed in menstrual tampons and pads, e.g., as an outer layer, or in bandages, compresses, rolls and the like. When formed of polymeric fibers it may be useful as a puff up cushion or pad. When formed, e.g., of air-laid fluff pulp, it is useful for incorporation as an absorbent center member in baby diapers and adult incontinent diapers, etc.

Referring to FIG. 18, in many instances it is desirable that two similar or dissimilar layers be brought into intimate relationship and this is admirably achieved by the structures shown. In certain instances, the outer layer 64 may be chosen for non-sticking contact with the skin of the user and to prevent sloughing off of fibers of the inner layer 62', while the inner layer may be formed of inexpensive substance. As one example, the outer layer may be a nonwoven of polymeric material that is hydrophobic (e.g., polyester) and the inner layer may comprise carded cotton or rayon or may comprise a single or multiple layers of inexpensive air-laid fluff pulp (formed of short length wood fibers). The support 60' may be open or closed depending upon its location and function in the overall article. It may be merely a permeable scrim, as where it lies over other absoptive components, 63, or it may form a baffle. It may, in some instances, itself be microundulated as the result of separate treatment or treatment in the assemblage.

FIG. 18 is also illustrative of a preferred form of puff pad in which the outer layer is chosen to be less extensible than the inner layer, to serve as a limiting means for the distension that occurs during tensioning activation of the article.

In one instance the inner layer may itself be subjected to a first stage microcompression pretreatment to bring it to a first level of bulkiness and compaction and then it may be assembled with the limiting layer and the two may be subjected to a second stage of micro-compression, as an assemblage, resulting in the form shown in FIG. 18 (for simplicity of illustration the first stage microundulations are omitted from the representation).

It will be noted that as a result of microcreping of the assemblage, the limiting layer is intimately united with the thicker inner layer 60'. Thus when repeated sudden tension is applied, e.g., by arrows in FIG. 18, not only does the limiting layer 64 limit the overall distension of the inner layer, see FIG. 19, but it also assures that the distension that does occur is distributed relatively uniformly across the entire inner layer, and thus avoids undue thinning and rupture at localized areas.

In the case, e.g., where the inner layer is comprised of relatively free, long fibers, 62a, a very remarkable increase in thickness, loftiness and softness may be achieved, as suggested in FIG. 19. Though, for simplicity of illustration in FIG. 19 the fibers 62 are shown relatively straight, it is readily possible to conduct the microprocessing so that a desirable degree of kinkiness is inherently retained in the individual fibers, to further contribute to the loftiness and softness of the pad.

The fibers of the puff pad may be polymeric and hydrophobic and serve as a comfortable non-moisture retaining outer layer lying over, e.g., layers of fluff pulp of various forms with or without the presence of superabsorptive substance.

In another case, the layer 62' can be comprised of absorbent fibers, and, desirably in some instances, superabsorbent substances can be adhered thereto and form a constituent part of the assemblage.

Figure 21:
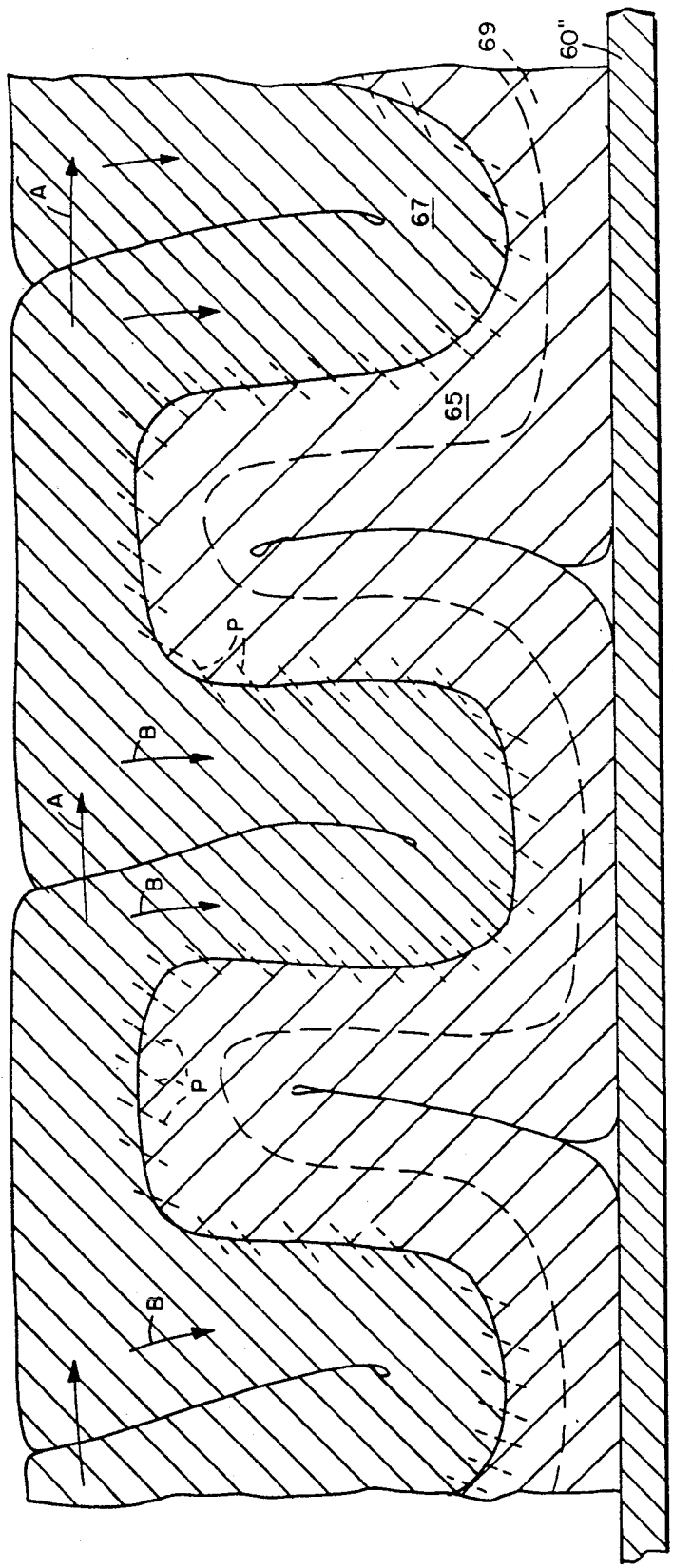
FIG. 21 is a cross-sectional view of the article of FIG. 20 shown with still further magnification.
Figure 20:
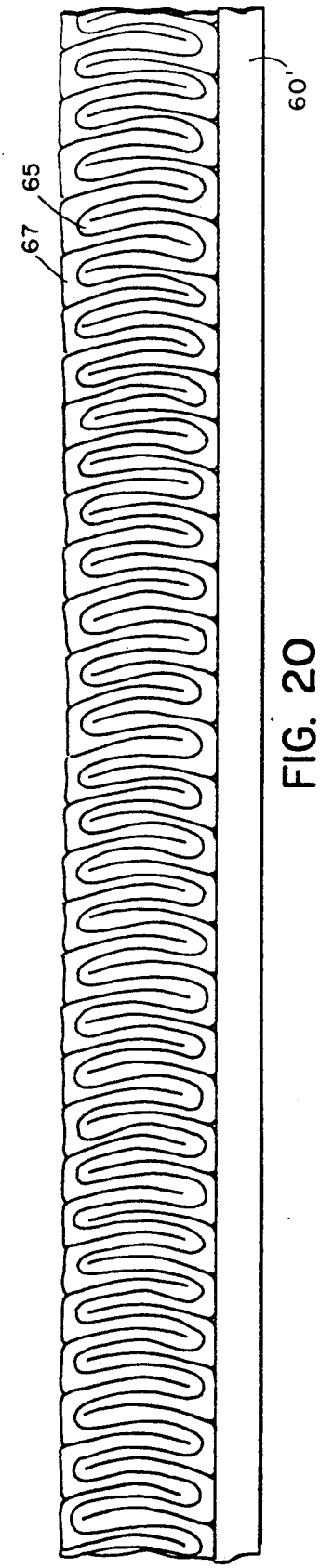
FIG. 20 is a magnified, diagrammatic cross-sectional view of an absorbent pad comprised of absorbent and super-absorbent layers.

Referring now to FIGS. 20 and 21, a microundulated assemblage of layers addresses a drawback encountered with superabsorbent materials. These materials, while having an ultimately very large liquid capacity, have a certain delay in accepting liquid, and do not distribute liquid well.

In FIGS. 20 and 21, layer 65 carries a superabsorbent substance. It may, for instance, comprise a pair of tissuelike layers between which is sandwiched a superabsorbent powder of one of the various kinds that are readily available. Layer 67 is comprised of highly absorbent fibers, for instance a bat of rayon or one or multiple layers of air laid fluff pulp.

The assemblage is in a mutually microundulated state in which the faces of the two sheets are tightly, intimately engaged, and with the sides of microundulation abutting one another.

The substance of the upper layer 67 defines a highly receptive reservoir for any sudden discharge of liquid and serves as a highly effective distributor even capable of having a manifold effect. Thus if liquid is applied to the outer face of layer 65 at a point to the left of the segment shown in FIG. 21, the liquid can be immediately conveyed to the right in short circuit path A from one undulation to the next and in branch path B down the sides of the undulation and then to a large facial area of the superabsorbent layer 65. Even when the undulations do not contact one another, a very fast single mode distributing effect can be achieved.

As suggested by the dotted lines, p, the process of microprocessing the assemblage of layers can result in the cross-entry of fibers from one layer to another, to a degree merging the two layers together to further enhance the liquid distribution.

In other cases a further distributing layer 69, a face of which is suggested by a dashed line in FIG. 21, can be provided on the lower side of the superabsorbent layer, mutually microprocessed in the assemblage, to serve as a reservoir on that side. In some cases it is advantageous to provide a distribution of openings through the superabsorbent layer to establish liquid communication between the two reservoir/distributors.

Figure 22:
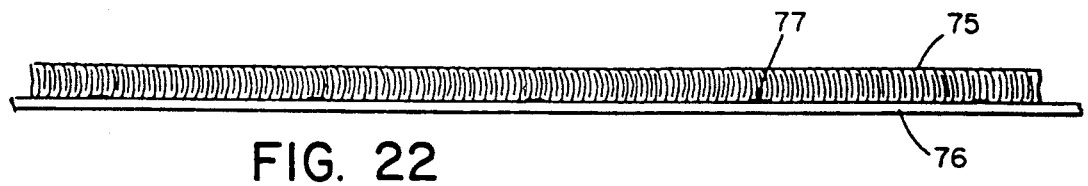
FIG. 22 is a magnified cross-sectional view of an absorbent pad having a predispositon to form macroundulations produced by a pattern of adhesive lines.
Figure 23:
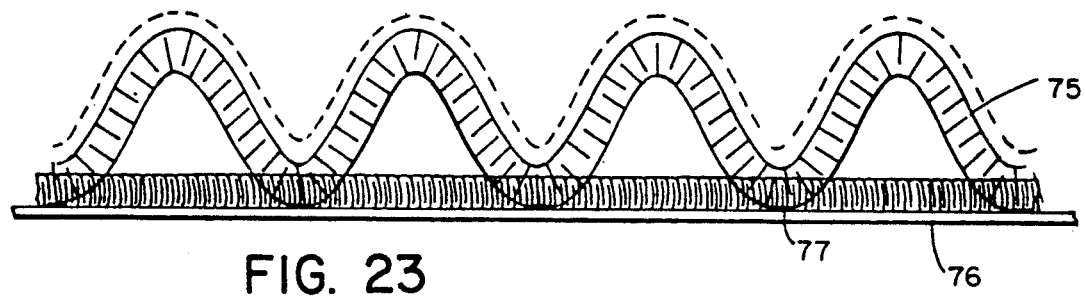
FIG. 23 is a diagrammatic view of the article of FIG. 22 illustrating the arched macroundulations formed in the article when wetted.

Referring now to FIGS. 22 and 23, a liquid activatable absorbent pad is illustrated. The microundulated sheet 75, formed, for instance, by multiple layers of air-laid fluff pulp, lies upon a support 76 which may be liquid impermeable and serves as a baffle. A pattern of spaced apart, parallel adhesive lines 77 is provided to anchor the layer 75 in those regions in a predetermined pattern chosen to establish a propensity for formation of macroundulation. By simple trial and error, a pattern can readily be determined for a given set of layer thickness, substance and degree of treatment parameters. Thus the compression effects produced in the lengthwise expanding web, on incidence of liquid, can create an arched formation, effectively thickening the pad and creating space for the retention of liquid. Superabsorbent substance may be included between baffle 76 and layer 75 which may swell to fill the void created by the arching layer.

As before, outer layers suggested by dashed lines, may be provided in the assemblage.

Figure 24:
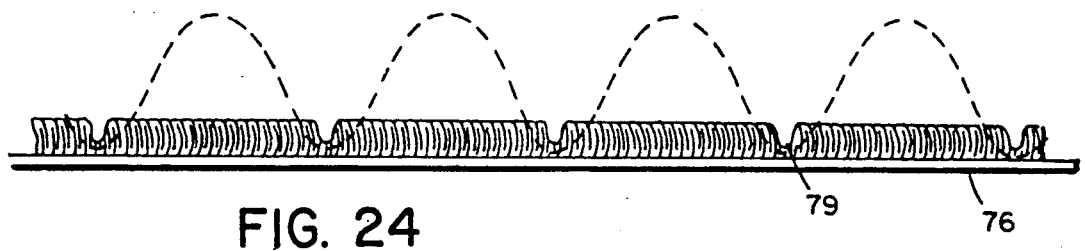
FIG. 24 is a diagrammatic view similar to FIG. 22 of another article provided with embossed lines in a pattern providing a disposition to form macroundulations.

Referring to FIG. 24, an alternate means of providing the desired disposition to form macroundulations is provided by the heavy embossing of parallel lines 79 in the microundulated layer. The resultant microundulations, formed when the layer is wetted, are suggested by the dashed lines in FIG. 24.

Other alternatives for providing the disposition to form macroundulations include end restraints or side restraints on the layer, and application of a coarse or double crepe to the layer.

Figure 25:
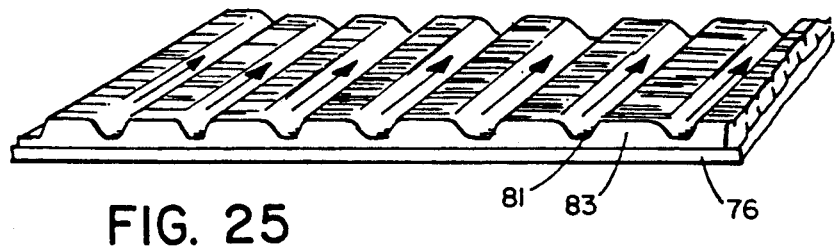
FIG. 25 is a plan view suggestive of the bands of relatively high and low density achieved in an article when employing the preferred forming process of the invention.

Referring to FIG. 25, a layer that has been microundulated in accordance with FIGS. 2-5 and incorporated in an absorbent article can serve an especially useful role in providing both distribution and reservoir effects. In the narrow regions of the matched larger rolls, the substance of the fibrous layer is of much greater density than is the density of the "lazy U's" formed of the same material in the relatively wider regions that correspond to the smaller disks of the matched serrated roll microcreper.

When exposed to liquid, the relatively dense regions enable an exceedingly fast transit velocity for liquid to be achieved, see arrows, FIG. 25, and thus in a short time liquid may, as desired, be distributed over a larger area in a series of bands. On the other hand, the bands of lazy "U's" adjacent to the high density bands define a very substantial interstitial volume that serves to readily receive the liquid from the lines of high velocity distribution. Thus this layer, in another way, has highly effective manifolding and storage effects. These features make it particularly advantageous to combine with a superabsorbent layer in line with the discussion above.

We claim:

1. A product comprising at least a first, longitudinally microundulated, shortened layer of fibers, said layer being further characterized by having at least 10 microundulations per inch in said longitudinal direction, said microundulations being in a longitudinally compressed-together relationship with adjacent microundulations having their sides abutting one another, said microundulated layer having a length at least 20% shorter than the lay-flat length of the layer when the layer is extended to cause said microundulations to lie substantially flat, said microundulated layer being shape-retentive when undisturbed and having stored mechanical energy capable, under activating conditions, to cause said product to expand.

2. The product of claim 1 wherein said layer comprises long fibers in a substantially unbonded state, the majority of which fibers extend in said longitudinal direction; said shortened, compressed-together relationship being in the direction of the length of the majority of said fibers.

3. The product of claims 2 or 1 wherein said layer is shape-retentive when dry with stored mechanical energy, said layer being capable of release of mechanical energy to expand when wetted, said layer being disposed on a liquid impermeable baffle, and means establishing a predisposition of the layer to expand with a regular series of macroundulations.

4. The absorbent product of claim 3 wherein said baffle comprises a liquid impermeable baffle member extending along one side of said layer, the layer being free to rise from said baffle member in spaced apart regions to form said macroundulations.

5. The absorbent product of claim 3 wherein said means for establishing said predisposition includes adhesive means securing said layer to said baffle in a pattern at periodic intervals that prevent longitudinal motion of the respective portions of said layer relative to said baffle in the manner that the layer when wet forms itself into a series of macroundulations each in the form of a single raised arch between periodic intervals where adhesive means secures said layer to said baffle.

6. The absorbent product of claim 3 wherein said means for establishing said predisposition includes a series of depression lines in said layer arranged such that the layer when wet forms itself into macroundulations in the form of respective arches between successive depression lines.

7. The product of claim 2 or 1 wherein said microundulated layer is shape-retentive and has stored mechanical energy capable, under activating conditions, to cause said product to expand, a relatively inextensible limiter member joined to said layer at least at closely spaced apart points along the length of said layer, said layer being adapted to puff up substantially in thickness in response to tensioning, said limiter member serving to distribute strain produced by said tensioning over the length of said layer to promote uniformity of puff-up.

8. The product of claim 7 produced by the process of subjecting said first layer to a first microcreping treatment, selecting a second layer as said limiter member, assembling said second layer face-to-face with said first layer after said first microcreping treatment to provide an assemblage, and subjecting said first layer and said second layer simultaneously to a second microcreping treatment to effectively join said second layer at closely spaced apart points to said first layer, the combined effect of said first and second microcreping treatments producing said microundulations in said first layer.

9. The product of claim 2 wherein said layer comprises a batt of substantially aligned fibers.

10. The product of claim 2 or 9 wherein said layer is comprised of rayon fibers.

11. The product of claim 2 or 9 wherein said layer is comprised of carded fibers.

12. The product of claim 11 wherein said layer is comprised of rayon fibers.

13. The product of claim 2 or 9 wherein said layer comprises a batt of absorbent fibers, and said layer is combined in an assemblage with a relatively thin outer wrapping layer, said microundulations being formed in the combined assemblage.

14. The product of claim 13 wherein said thin layer is hydrophobic.

15. The product of claim 14 wherein said first, microundulated layer of absorbent fibers is free to puff up in thickness under tension applied in the direction of the length of the majority of the fibers.

16. The product of claim 2, 9 or 1 wherein superabsorbent substance is incorporated therein.

17. The product of claim 16 wherein said superabsorbent substance is carried in a second layer that is combined in an assemblage with said first layer, said microundulations being formed in the combined assemblage whereby the superabsorbent substance-containing layer extends in intimate face-to-face relationship with said first layer.

18. The product of claim 17 wherein fibers of said first layer are merged into said second layer.

19. The product of claim 2, 9 or 1 wherein said first, microundulated layer comprises absorbent fibers, said layer disposed in face-to-face fluid transfer relationship with a different, fluid absorbent material.

20. The product of claim 19 wherein said different material includes a superabsorbent substance.

21. The product of claim 2, 9 or 1 wherein said first layer is one of multiple overlying layers of absorbent material, at least a plurality of said layers including said first layer being in said shortened longitudinally microundulated state.

22. The product of claim 21 wherein said overlying layers comprise successive turns of a microundulated sheet-form member that has been rolled.

23. The product of claim 1 wherein said layer comprises air-laid fluff pulp.

24. The product of claim 1 wherein said layer is free from restraint that would prevent rapid expansion of said layer when subjected to a predetermined condition.

25. The product of claim 24 wherein said layer is comprised of absorbent fibers and said layer is adapted to expand in response to contact with fluid.

26. The product of claim 24 sized, shaped and constructed to serve as a pad for absorbing fluid discharge from the body.

27. The product of claim 26 wherein said pad includes a fluid-impenetrable baffle along one side of said layer, and the other side is exposed to receive said fluid.

28. The product of claim 1 having oppositely directed faces wherein said layer is free from face-wise restraint that would prevent said layer from puffing up substantially in thickness in response to tensioning.

29. The product of any of the claim 28 wherein said layer is comprised substantially of polymeric fibers and said product, when puffed up, is adapted to provide a cushioning effect.

30. The product of any of the claim 28 wherein said layer is comprised of absorbent fibers and fluid-retentive volume of said layer.

31. The product of claim 28 in the form of an absorbent pad for use with the body, said product including a fluid-impermeable baffle extending along said layer to confine liquid to said layer.

32. The product of claim 28 including limiter means for limiting the degree of extension of said layer during said tensioning.

33. The product of claim 32 wherein said limiter means comprises a member which is less extensible than said layer, said limiter means being joined at least at closely spaced apart points to said layer along the length of said layer.

34. The product of claim 33 produced by the process of subjecting said first layer to a first microcreping treatment, selecting a second layer as said limiter means, assembling said second layer face-to-face with said first layer after said first microcreping treatment to provide an assemblage, and subjecting said assemblage of said first layer and said second layer to a second microcreping treatment to effectively join said second layer at closely spaced apart points to said first layer, the combined effect of said first and second microcreping treatments producing said microundulations in said first layer.

35. The product of claim 32 wherein said limiter means comprises a thin outer covering layer.

36. The product of claim 32 wherein said limiter means is a limiter layer incorporated in said product.

37. The product of claim 32 wherein said layer is comprised substantially of polymeric fibers and said product, when puffed up, is adapted to provide a cushioning effect.

38. The product of claim 37 shaped to serve as a pillow when puffed up.

39. The product of claim 37 wherein said layer is hydrophobic and lies over an absorbent layer, said hydrophobic layer being exposed for a cushioning relationship to a part of the body, said hydrophobic layer being rapidly permeable to body fluids passing from the body to said absorbent layer.

40. The product of claim 32 wherein said layer is comprised of absorbent fibers and said puffing-up is adapted to enlarge the fluid-retentive volume of said layer.

41. The product of claim 32 in the form of an absorbent pad for use with the body, said product including a fluid-impermeable baffle extending along said layer to confine liquid to said layer.

42. The product of claim 41 in the form of a pad that is highly compact during storage and is constructed to be puffed up prior to use by application of tension.

43. The product of claim 41 sized, shaped and constructed to serve as a menstrual pad.

44. The product of claim 1 including at least a second layer, said first microundulated layer formed of absorbent fibers and the second layer including superabsorbent substance, said second layer being longitudinally microundulated so that it is shorter than its lay-flat length in a direction corresponding to the direction of shortness of said first layer, the superabsorbent substance-containing layer extending in face-to-face relationship with said first layer.

45. The absorbent product of claim 44 wherein said absorbent layer is adapted to receive, distribute and temporarily store a discharge of liquid and introduce it to said superabsorbent substance for take-up.

46. The absorbent product of claim 44 formed by the process of combining said layers prior to microundulations having been provided in said layers, and treating said combined assemblage by a matched, serrated roll microcreper to produce said microundulations in both of said layers.

47. The product of claim 44 wherein said first layer comprises a paper-like layer formed of short wood fibers.

48. The product of claim 47 wherein said first layer comprises air laid fluff pulp.

49. The product of claim 44 wherein said first layer contains a substantially larger number of microundulations than said second layer.

50. The product of claim 44 wherein, over the mutual extent of said layers, fibers of said first layer are merged into the body of said second layer.

51. The product of claim 1 in the form of an absorbent product, said layer being of sheet-form, and having a distribution of highly densified bands separated by bands of lesser density.

52. The product of claim 51 wherein said distribution is the result of being treated by a matched, serrated roll microcreper.

53. The product of claim 51 or 52 wherein said layer is disposed in face-to-face fluid transfer relationship with a different material, said highly densified bands forming distribution channels for rapid distribution of liquid and said bands of lesser density providing reservoirs for receiving liquid from said distribution channels.

* * * * *